United States Patent
Bi et al.

(10) Patent No.: US 6,246,745 B1
(45) Date of Patent: Jun. 12, 2001

(54) METHOD AND APPARATUS FOR DETERMINING BONE MINERAL DENSITY

(75) Inventors: Xiaoli Bi, Cerritos; David Edelstein, Manhattan Beach; Brent J. Liu, Los Angeles; Louai Al-Dayeh, Hermosa Beach, all of CA (US)

(73) Assignee: CompuMed, Inc., Los Angeles, CA (US)

( * ) Notice: Subject to any disclaimer, the term of this patent is extended or adjusted under 35 U.S.C. 154(b) by 0 days.

(21) Appl. No.: 09/430,053

(22) Filed: Oct. 29, 1999

(51) Int. Cl.$^7$ .................................................. G01N 23/04
(52) U.S. Cl. .............................................. 378/54; 382/132
(58) Field of Search .................................. 378/54, 12, 22, 378/45, 50, 83; 382/132, 259, 256

(56) References Cited

U.S. PATENT DOCUMENTS

| | | |
|---|---|---|
| 4,721,112 | 1/1988 | Hirano et al. ............... 128/659 |
| 5,241,406 | 8/1993 | Johnston et al. ............ 358/487 |
| 5,270,651 * | 12/1993 | Wehri ........................ 324/308 |
| 5,272,760 | 12/1993 | Echerer et al. .................. 382/6 |
| 5,291,537 | 3/1994 | Mazess ........................ 378/54 |
| 5,335,260 | 8/1994 | Arnold ...................... 378/207 |
| 5,365,564 | 11/1994 | Yashida et al. ............... 378/55 |
| 5,381,245 | 1/1995 | Johnston et al. ............ 358/487 |
| 5,384,862 | 1/1995 | Echerer et al. .................. 382/6 |
| 5,418,373 * | 5/1995 | Shimura ..................... 250/583 |
| 5,426,709 * | 6/1995 | Yoshida et al. .............. 382/132 |
| 5,533,084 | 7/1996 | Mazess ........................ 378/54 |
| 5,574,803 | 11/1996 | Gaborski et al. ............ 382/259 |
| 5,583,663 | 12/1996 | Boeve ....................... 358/487 |
| 5,671,070 | 9/1997 | Przybylowicz et al. ...... 358/487 |
| 5,673,298 | 9/1997 | Mazess ........................ 378/54 |
| 5,696,805 | 12/1997 | Gaborski et al. .............. 378/54 |
| 5,712,892 | 1/1998 | Weil et al. ..................... 378/54 |
| 5,734,740 | 3/1998 | Benn et al. .................. 382/132 |
| 5,785,656 | 7/1998 | Chiabrera et al. ........... 600/449 |
| 5,852,647 | 12/1998 | Schick et al. ................ 378/53 |
| 5,898,753 | 4/1999 | Schick et al. ................ 378/54 |
| 5,910,972 | 6/1999 | Ohkubo et al. .............. 378/54 |
| 5,917,877 | 6/1999 | Chiabrera et al. ........... 378/5.3 |
| 5,917,929 | 6/1999 | Marshall ..................... 382/128 |

OTHER PUBLICATIONS

Hyeonjoon Shim, Brent J. Liu, Ricky K. Taira, Theodore Hall, "Object–oriented approach towards the automatic segmentation of bones from pediatric hand radiographs," SPIE vol. 3034 0277–786X/97, pp. 95–105.

Brent J. Liu, Ricky K. Taira, HyeonJoon Shim, Patricia Keaton, "Automatic Segmentation of bones from digital hand radiographs," SPIE vol. 2434 0–8194–1782–3/95, pp. 659–669.

\* cited by examiner

*Primary Examiner*—Robert H. Kim
*Assistant Examiner*—Ivakli Kiknadre

(57) ABSTRACT

A method and apparatus for measuring bone density in a body part. The method and apparatus receive and process a digital image that includes at least one digit, a calibration wedge, and a target bone to compute the density of the target bone. Based on the digital image, a contour for the digit and the target bone are automatically extracted and displayed for the user. A user is then provided an opportunity to input information via an easy-to-use graphical user interface. The contour of the target bone is then automatically re-computed based on the user input. Then, the bone mineral density of the target bone is computed based on the re-computed contour of the target bone.

20 Claims, 17 Drawing Sheets

OSTEOGRAM REPORT                    COMPUMED INC.

TUESDAY, OCTOBER 19, 1999 12:50

NAME:
ADDRESS:
CITY:
STATE:       ZIP CODE:
ID:
SS#:
AGE AT MENOPAUSE:      SEX:   F
                       ETHNIC:
BIRTH DATE: 10/19/49   HEIGHT:
TEST#:      0000       WEIGHT:
COMMENT:               AGE:       50
                       X-RAY DATE: 10/19/99

| NORMAL BONE DENSITY |
| T-SCORE = 0.6 |

| DATE | BMD INDEX | T-SCORE |
|------|-----------|---------|
| 10/19/99 | 117.7 | 0.6 |

(1) T-SCORE = STANDARD DEVIATIONS
    ABOVE OR BELOW MEAN BMD
    FOR YOUNG NORMALS
    (20-50 YEARS OLD)
(2) BMD = BONE MINERAL
    DENSITY

SKELETAL STATUS

PHYSICIAN NOTES:

| T-SCORE RANGE | SKELETAL STATUS |
|---------------|-----------------|
| -1.0 OR ABOVE | NORMAL |
| -1.0 TO -2.5 | LOW BONE MASS (OSTEOPENIA) |
| -2.5 OR BELOW | OSTEOPOROSIS |

FIG. 18

METHOD AND APPARATUS FOR DETERMINING BONE MINERAL DENSITY

BACKGROUND OF THE INVENTION

1. Field of the Invention

The present invention relates to a method and apparatus for measuring the density of bones. More specifically, it relates to a method and apparatus for measuring bone mineral mass using radiographic absorptiometry.

2. Background of the Invention

Osteoporosis is a bone disease characterized by low bone mass and microarchitectural deterioration of bone tissue. This disease subjects a person to enhanced bone fragility and a consequent increase in fracture risk, particularly in the spine, hip and wrist. Osteoporosis is particularly common in postmenopausal women because their bone loss greatly exceeds that of men at this age. It has been estimated that at least 28 million Americans, 80% of whom are women, have a lower than normal bone mass and are at risk of having osteoporosis. In the United States alone, 10 million people already have osteoporosis and many women die each year from complications due to osteoporosis.

The assignee of the present invention has developed a proprietary bone density measurement system called Osteo-Gram Analysis. The OsteoGram Analysis system involves taking a standard X-ray of three fingers, along with a calibration wedge in the field of view by using existing and widely available standard X-ray equipment. The calibration wedge is utilized to adjust for differences among X-ray equipment, exposures, types of film, and the development process. The assignee of the present invention has a central specialized laboratory that receives these x-rays and provides a service to medical professionals of providing a bone mineral density (BMD) report based on the x-ray.

Although this service provides accurate reports, there has been a demand for an on-site solution that can be utilized by physicians or other medical professionals locally at their offices to generate the BMD report based on hand x-rays. Unfortunately, such a solution must overcome many difficult challenges, described below. Although there are piece-meal attempts to develop such a solution (see, e.g., U.S. Pat. Nos. 5,712,892 and 5,696,805), a complete solution has not been developed and has been elusive until now.

The first challenge is that the hardware needs to be simplified and reduced in cost, yet provide the same level of accuracy as the specialized custom hardware of the central laboratory. For example, the U.S. Pat. No. 5,712,892 utilizes CCD photodetector arrays to digitize the radiograph. The digitization results are excellent. However, it is cost prohibitive as an on-site solution and requires additional equipment to keep the arrays cool.

The second challenge is to develop new software that does not require the intervention and judgment of a trained technician. The equipment for the OsteoGram service is typically complex, and the intermediate segmentation results must be interpreted and verified by a skilled person (e.g., a laboratory technician with specialized training). The requirement of a trained technician results in added costs to train and employ these technicians. It is certainly cost prohibitive for each medical professional to hire a technician to work in their office.

The third challenge is to develop an easy-to-use graphical user interface that is intuitive, easy to learn, and that requires minimal set-up and learning time. For example, the U.S. Pat. No. 5,696,805 does not provide any graphical user interfaces, nor does it even allow for user input. In fact, it appears that the method of U.S. Pat. No. 5,696,805 does not even display the contours to the user, but instead the figures of this patent merely illustrate output data results from screen dumps of an image at pre-determined points in the program only to show a proper execution of the program.

The fourth challenge is to generate the BMD in a timely manner so that a medical professional can provide a report of the results in a matter of a few minutes while the patient is still in the office. As a point of comparison, the processing that occurs in the central laboratory can take more than half an hour of processing time in addition to time needed by a technician to verify and correct the output or otherwise aid the system. Only then can results be sent back to the client.

Accordingly, it would be advantageous to have a solution that makes BMD testing and report as simple as taking a patient's temperature or blood pressure reading. No previous systems exist, however, that can provide a measure of bone density with minimum human intervention by simply scanning in an x-ray with a desktop scanner and running a program with an easy-to-use and intuitive graphical user interface on a personal computer (PC).

Other Bone Assessment Devices

Various devices for measuring the content of bone have been known for a number of years, and by way of example, several forms of these devices can be found in U.S. Pat. Nos. 5,712,892, 5,785,656, and 5,917,877. U.S. Pat. No. 5,785,656 is directed towards a bone assessment device that utilizes ultrasound technology. Although this technology has potential for providing bone mass measurements, it has not matured and faces several un-resolved technical hurdles. For example, it is yet to be determined which features of ultrasound velocity and attenuation are related to bone density, which features of velocity and attenuation reflect bone architecture, and how these features can be combined to estimate bone mass.

U.S. Pat. Nos. 5,712,892 and 5,917,877 are directed towards bone measurement devices that utilize an X-ray beam for acquiring data. Unfortunately, these devices are complex to implement, costly to manufacture, and generally require substantial training before users can competently operate the devices.

Accordingly, there remains a need for an improved method and apparatus for generating a bone mineral density report based on a radiograph of a patient's hand that departs significantly from existing systems.

SUMMARY OF THE INVENTION

Accordingly, it is an object of the present invention to provide a radiographic absorptiometry device that is easy-to-use and does not require specialized training.

It is also an object of the present invention to provide a radiographic absorptiometry device that utilizes cost-effective digitizing equipment.

It is also an object of the present invention to provide a radiographic absorptiometry device that provides an automated quality assurance module for ensuring the quality of the index of bone density.

It is another object of the present invention to provide a radiographic absorptiometry device that automatically generates accurate and consistent bone mineral density reports without user intervention.

It is yet another object of the present invention to provide a radiographic absorptiometry device that employs an improved and automated bone mineral density analysis module that more accurately determines the mass and volume of a target bone thereby leading to a more accurate bone mineral density result.

It is a further object of the present invention to provide a radiographic absorptiometry device that automatically determines and displays contours of the finger, the bones of the finger, and the wedge.

It is a further object of the present invention to provide a radiographic absorptiometry device that employs an easy-to-use graphical user interface for allowing a user to review the automatically generated contours, and if the user is not satisfied, to provide further information that is used by the present invention to refine the contour of the bone.

It is another object of the present invention to provide a radiographic absorptiometry device that includes an easy-to-use drawing tools for allowing a user to selectively modify the contours of the bones of the fingers without affecting the other portions of the image.

It is another object of the present invention to automatically re-calculate and re-display a contour of a bone based on user input.

It is yet another object of the present invention to provide a graphical user interface that allows a user to specify a top joint space location and a bottom joint space location by pointing and clicking on the desired points, which are in turn utilized by the present invention to generate the bone contour.

It is yet another object of the present invention to provide a graphical user interface for allowing a user to selectively modify the specified top and bottom joint space locations by incrementing on a pixel-by-pixel basis to refine a bone contour.

In accordance with the present invention, the foregoing objects are met in a radiographic absorptiometry device for providing an index of bone mineral density from a radiograph. The radiographic absorptiometry (RA) device includes a personal computer (PC), a digital scanner, and bone mineral density measurement software (BMDMS) executing on the PC, and a printer. Bone mineral density measurement software (BMDMS) includes a segmentation module for automatically generating a contour of the wedge and middle phalanges and a BMD analysis module for generating an index of bone density based on the contours provided by the segmentation module and BMD report.

In one embodiment, BMDMS automatically determines the contours of the fingers and wedge, extracting these features from the remainder of the image, and displaying these contours to the user.

In another alternative embodiment, BMDMS provides a build-from-raw graphical user interface for allowing a user to double click anywhere on the wedge for the BMDMS to automatically create a wedge contour or outline. The build-from-raw graphical user interface also allows a user to use the Click Top/Click Bottom feature to provide a point related to the top joint space and a point related to the bottom joint space. Based on these two points, the BMDMS generates a contour of the bone, such as the middle phalange.

In an alternative embodiment, BMDMS provides user intervention tools that allow a user to provide information to the BMDMS so that BMDMS can dynamically re-calculate and display the contours based on the information. For example, the BMDMS provides a Click Top/Click Bottom graphical user interface for allowing the user to specify top and bottom joint space locations with a user input device, such as a mouse. In addition, the BMDMS provides a fine-tune window graphical user interface for allowing the user to selectively adjust a top or bottom joint space point on a pixel-by-pixel basis. The selection can be made by a mouse or by the Up and Down arrows on a keyboard. When selected, a popup window that displays an enlarged portion of the bone of interest and two sets of Up and Down arrows are provided. One set corresponds to the top joint space, and the other set corresponds to the bottom joint space. Every time a user clicks on one of these buttons, BMDMS dynamically (1) captures the user input, (2) re-calculates the bone contour, and (3) re-displays the new contour for each click of the Up or Down arrow in real time.

In an alternative embodiment, if all the above-described semi-automatic methods fail to produce an acceptable result, the present invention provides an easy-to-user graphical user interface for allowing the user to selectively modify these displayed contours without being able to affect the remainder of the image. For example, a pencil icon is provided for a user to re-draw portions of the bone contour with affecting the remainder of the image. An eraser icon is also provided for a user to erase only portions of the bone contour without affecting the remainder of the image.

In another alternative embodiment, BMDMS provides a database for allowing a user to input, save, retrieve, edit, or delete patient and physician information related to the BMD report.

BRIEF DESCRIPTION OF THE DRAWINGS

FIG. 18 illustrates an exemplary report that can be generated by the system of th present invention.

DETAILED DESCRIPTION OF THE INVENTION

Figure 1:
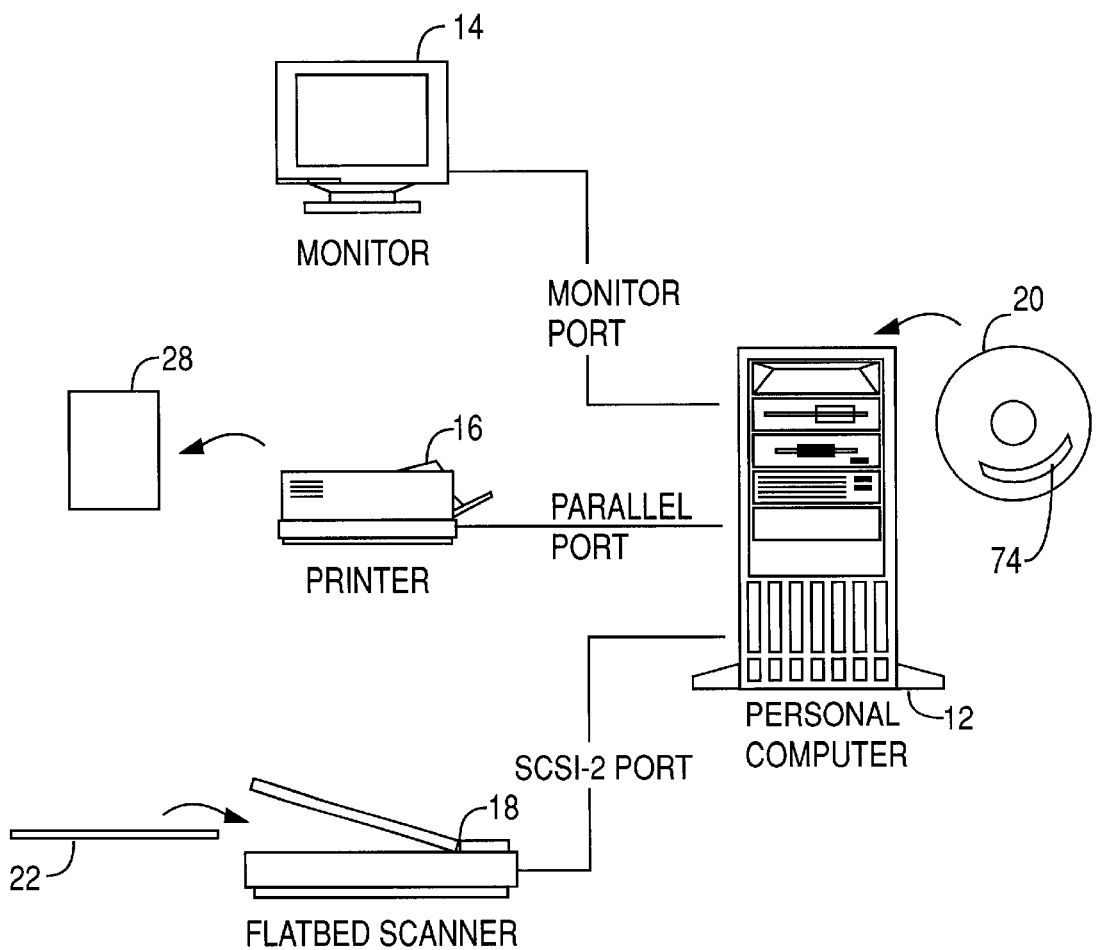
FIG. 1 illustrates a bone mineral density measurement system configured in accordance with one embodiment of the present invention.

The subject invention will be described with reference to numerous details set forth below, and the accompanying drawings will illustrate the invention. The following description and the drawings are illustrative of the invention and are not to be construed as limiting the invention. Numerous specific details are described to provide a thorough understanding of the present invention. However, in certain instances, well known or conventional details are not described in order to not unnecessarily obscure the present invention in detail. In the drawings, the same element is labeled with the same reference numeral.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. Copyright© COMPUMED, Inc. 1999.

The present invention provides (1) a novel and accurate bone mineral density calculation module; (2) novel user intervention tools and graphical user interfaces for allowing a user to easily provide input to the system; (3) an automatic segmentation module for applying image processing and shape analysis to automatically segment the contour of the hand, wedge, and target bones; (4) a novel desktop scanner calibration module that allows a desktop scanner to be used to digitize radiographs for bone-densitometry purposes; and (5) a bone mineral density report generation module.

PC-Based Radiographic Absorptiometry Device (RAD) With A Scanner

FIG. 1 illustrates a bone mineral density measurement system 10 (also referred to herein as a radiographic absorptiometry device (RAD)) configured in accordance with one embodiment of the present invention. The system 10 has a personal computer (PC) 12 that is coupled to a monitor 14, a printer 16, and a scanner 18 through a monitor port, a parallel printer port, and a scanner port (e.g., a SCSI port), respectively. Printer 16 can be any output device, such as a thermal printer, dot matrix printer, laser printer, and ink jet printer.

A computer readable medium 20, such as a CD-ROM, has a bone mineral density measurement software (BMDMS) 74 of the present invention stored thereon. BMDMS 74 can be loaded into and run on PC 12. BMDMS 74 is described in greater detail hereinafter with reference to FIG. 5.

In this embodiment, the present invention utilizes properly qualified and calibrated commercial flatbed scanners 18 that are inexpensive, amendable to an on-site solution, not susceptible to operator error, and immune to ambient light noise while generating digitized radiographs comparable to the output obtained by CCD cameras.

A novel aspect of the present invention is the validation of using a flatbed scanner (e.g., a commercial grade scanner) to digitize medical radiographs for bone densitometry purposes. In this regard, the present invention identifies the requirements for digitizing a radiograph in general and specifically the requirements for using a digitized radiograph for bone densitometry purposes. In addition, the present invention specifies scanner settings and other scanning parameters, described below. These settings and parameters, when adhered to, cause the image characteristics obtained by the flatbed scanners to become comparable to those obtained with laboratory-grade CCD-cameras. These parameters and setting are described in greater detail hereinafter.

Alternatively, the scanner 18 can be replaced with a digitizer for converting analog information into digital information. For example, the digitizer can be a CCD camera or other device for digitizing the radiographs (i.e., converting radiographs into digital images suitable for image processing). By scanning the x-ray film, the digitizer turns the radiographic optical density information into digital information. The resulting digital form (gray scale image) includes a plurality of minute squares (called pixels) each representing one unit area in the original film and having one gray shade value.

Figure 2:
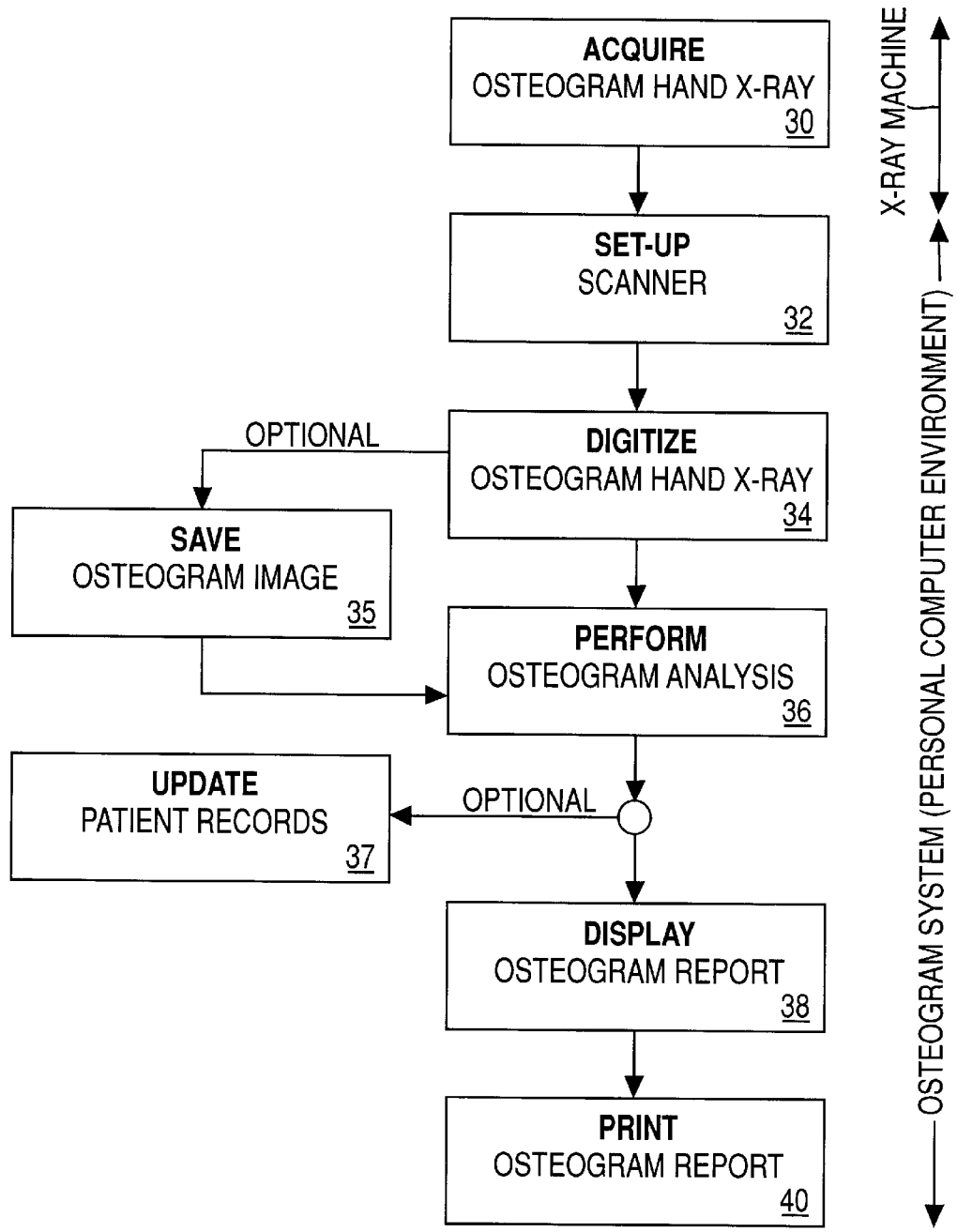
FIG. 2 is a flowchart illustrating the steps of a method for measuring the bone mineral density of a target bone according to one embodiment of the present invention.

FIG. 2 is a flowchart illustrating the steps of a method for measuring the bone mineral density of a target bone according to one embodiment of the present invention. In step 30, a radiograph 22 is acquired by utilizing a standard x-ray machine with a low level of radiation. One advantage of the present invention is that a patient need be subject only to a low-dose of radiation as compared to other systems, such as dual energy x-ray absorptiometry DEXA systems.

Figure 3:
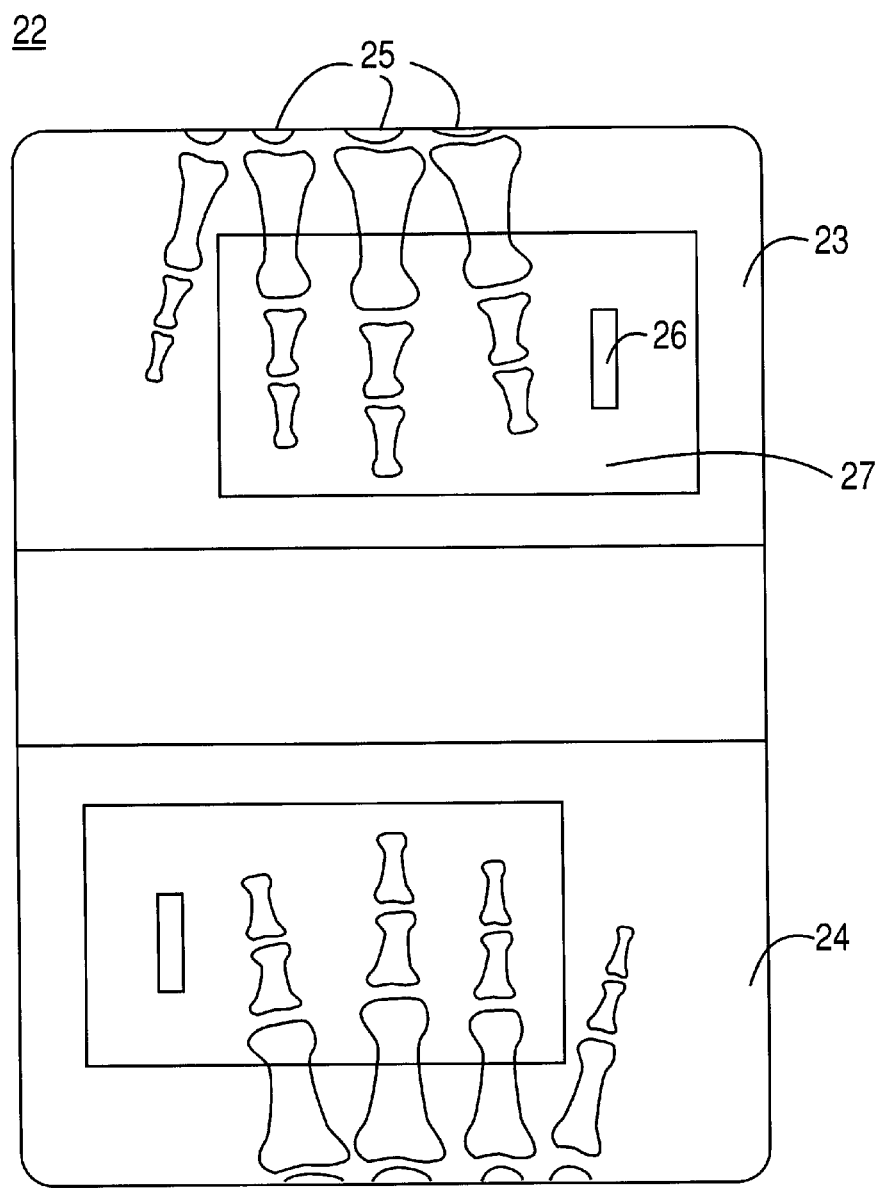
FIG. 3 illustrates a radiograph that can be input into the system of FIG. 1.

FIG. 3 illustrates an exemplary radiograph 22 that can be inputted into the system of FIG. 1. The exemplary radiograph has two exposures 23, 24 with each exposure having three digits of a hand and a calibration wedge. For example, the first exposure 23 has three digits 25 and a calibration wedge 26. When a scanner 18 is used to input the radiograph 22, a user can designate a region of interest (e.g., region 27) for each exposure by using the driver program for the scanner 14. Alternatively, if the radiograph 22 is digitized by using other equipment, such as a CDD camera, then the user focuses or otherwise controls the equipment to specify a region of interest.

In step 32, a user sets up the scanner 18. In step 34, the x-ray 22 is digitized. In step 35, the digitized image is optionally saved. In step 36, a bone mineral density result is automatically generated. The result can be a bone mineral density index, which can be described in a report 28. An example of the format of the report 28 is described in greater detail hereinafter with reference to FIG. 18. In step 37, the patient record, associated with the radiograph 22, can be optionally updated. In step 38, the BMD result and/or report can be displayed on the monitor 14. In step 40, the report 28 can optionally be printed by the printer 16.

Figure 4:
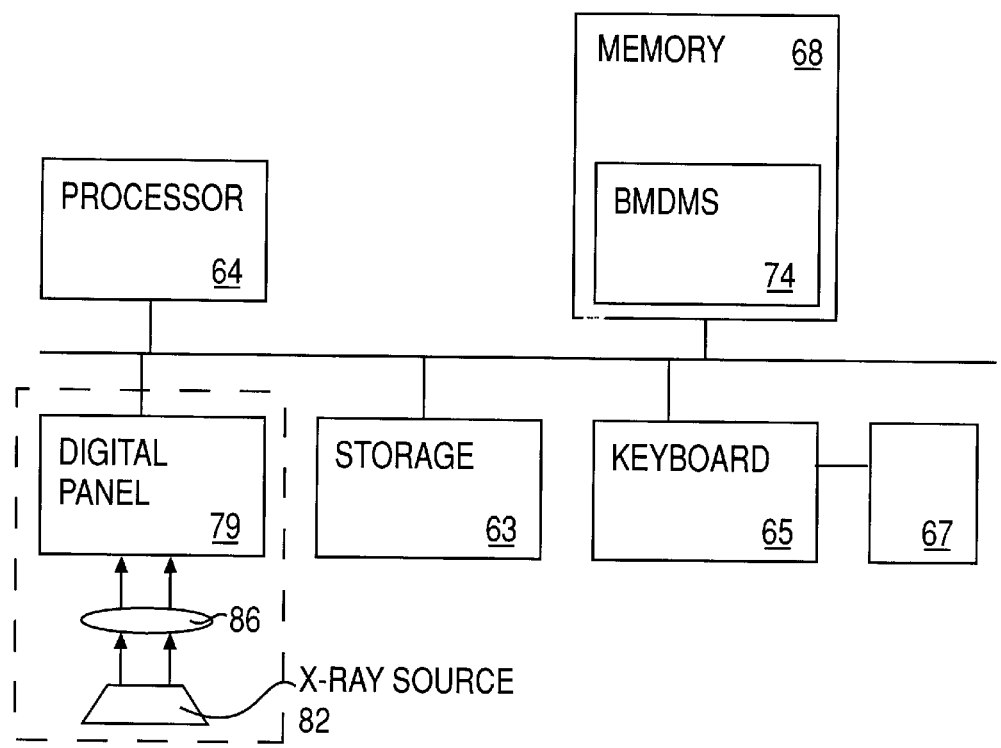
FIG. 4 is a block diagram illustrating in greater detail the personal computer of FIG. 1.

FIG. 4 is a block diagram illustrating in greater detail the personal computer 12 of FIG. 1. The PC 12 includes a processor 64 that is coupled to a user input device 65, such as a keyboard, for allowing a user to input information and a cursor pointing device 67, such as a mouse, track-ball, or touch pad. PC 12 also has a memory 68 for storing programs, such as bone mineral density measurement software (BMDMS) 74 of the present invention, and a storage device 63, such as a hard disk.

The PC 12 includes a memory 68, such as random access memory (RAM), that includes BMDMS 74 of the present invention. The PC 12 can also include a storage 63 that can be a mass memory (such as a hard magnetic disc or CD ROM) for storing digital images, application programs, driver programs, a database with patient information and bone density results. Components 63, 64, 65, 68, 67, and 79 can be connected together by control/data bus 62.

The PC 12 can also include a transportable storage medium drive (not shown) for reading from and/or writing to transportable storage media, such as a floppy magnetic disk or writable optical compact disk (CD).

As used in this application, computer readable storage medium can include, for example, magnetic storage media, such as magnetic disk (hard drive, floppy disk) or magnetic tape; optical storage media, such as optical disk, optical tape, or machine readable bar code; solid state electronic storage devices, such as random access memory (RAM), read only memory (ROM); or any other physical device or medium which can be employed to store a computer program.

Stand-Alone Radiographic Absorptiometry Device (RAD) With A Filmless X-Ray System In an alternative embodiment, system 10 can use a filmless x-ray system 79 instead of the scanner 18. The filmless x-ray system 79 directly converts x-rays into a digital image without film. X-ray system 79 uses x-rays to image a patient's hand and directly generates a corresponding digital image. Filmless x-ray system 79 can include an x-ray source 82 for generating x-rays, a digital panel 84 that includes an array of detectors for detecting the x-rays and generating a digital image corresponding to an object 86, which can be a body part extremity, such as a hand or foot, being imaged. In this embodiment, system 10 can be implemented in a stand-alone radiographic absorptiometry device (RAD) with a filmless x-ray system 79 while FIG. 1 illustrates the radiographic absorptiometry device (RAD) as implemented by the personal computer (PC) 12 coupled to the scanner 18.

The method of the present invention is performed on a digital image of a body part extremity having digits (e.g., a hand with fingers). The digital image can be generated by the scanner 18 of FIG. 1 or the filmless x-ray system 79 of FIG. 4. In addition, the present invention can process digital images generated by other image acquisition systems that can include, but is not limited to, (1) a standard x-ray screen/film combination which produces an x-ray film image which is processed chemically or thermally and the processed film digitized by a scanner or digitizer; (2) a computed radiography (CR) system where a latent x-ray image is formed in a storage phosphor and a corresponding digital image is produced by reading out the storage phosphor by a CR reader; (3) a direct digital acquisition system typically consisting of a phosphor based scintillating screen coupled to an imager through a lens or fiber optic system. Although the image acquisition systems described above generate planar images, the system of the present invention can be configured to process cross-sectional images (such as MRI, CT, US, and PET images).

The processor 64 when executing the BMDMS 74 of the present invention performs image processing on the received digital image for bone density calculation purposes. It is noted that one or more of the steps of the method of the present invention can be carried out using software routines. The processor 64 can also include hardware or firmware for carrying out one or more of said method steps. Thus, the steps of the method of the invention can be carried out using software, firmware, and hardware, either alone or in any preferable combination.

Qualification and Calibration of Scanner 18

For example, for the BMD evaluation purposes of this invention, a flatbed scanner is considered adequate for radiographic absorptiometry bone density analysis when the following predetermined parameters are met: 12-bit pixel depth, optical density in the range of 0 OD to 3 OD, scanning resolution of at least 231 Dots Per Inch (DPI), linearity errors <3%, mean stability over one hour better than 1%, and a 8"×10" minimum scan area for transparencies.

Some common characteristics of the qualified scanners include (1) is commercially available ("off-the-shelf") and utilizes a commercially available device driver; (2) requires a one pass scan; (3) can connect directly to RAD 60; (4) can be utilized by the software, of the present invention, to measure and accommodate small-scale errors; and (5) utilizes an enclosed transparency adapter to eliminate room-light interference.

The present invention clearly specifies a method for calibrating the qualified flatbed scanners to produce consistent Bone-Mineral-Density (BMD) results that are independent of the manufacturer or model of the scanner.

In one embodiment, the following scanner settings or parameters are automatically pre-set by the present invention in the scanner control software (e.g., scanner driver): (1) dimensions of the output image; (2) dimensions of the pixels; (3) image type as gray scale; (4) dynamic range of gray-scale as 12-bit (4095 gray scales); and (5) gray-scale response. For example, the present invention can use a look-up table to store pre-defined scanner settings for each qualified scanner and automatically pre-set the scanner driver with these values. The step, performed by the present invention, of automatically pre-setting these predetermined parameters is described in greater detail with reference to step 119 of FIG. 6.

The gray-scale response is a look-up table that describes the mapping from optical densities (OD) in radiographs to fixed pixel intensities in digitized images. This parameter is controlled by the present invention to achieve the proper characteristics of the digital image that is required for bone densitometry.

Figure 5:
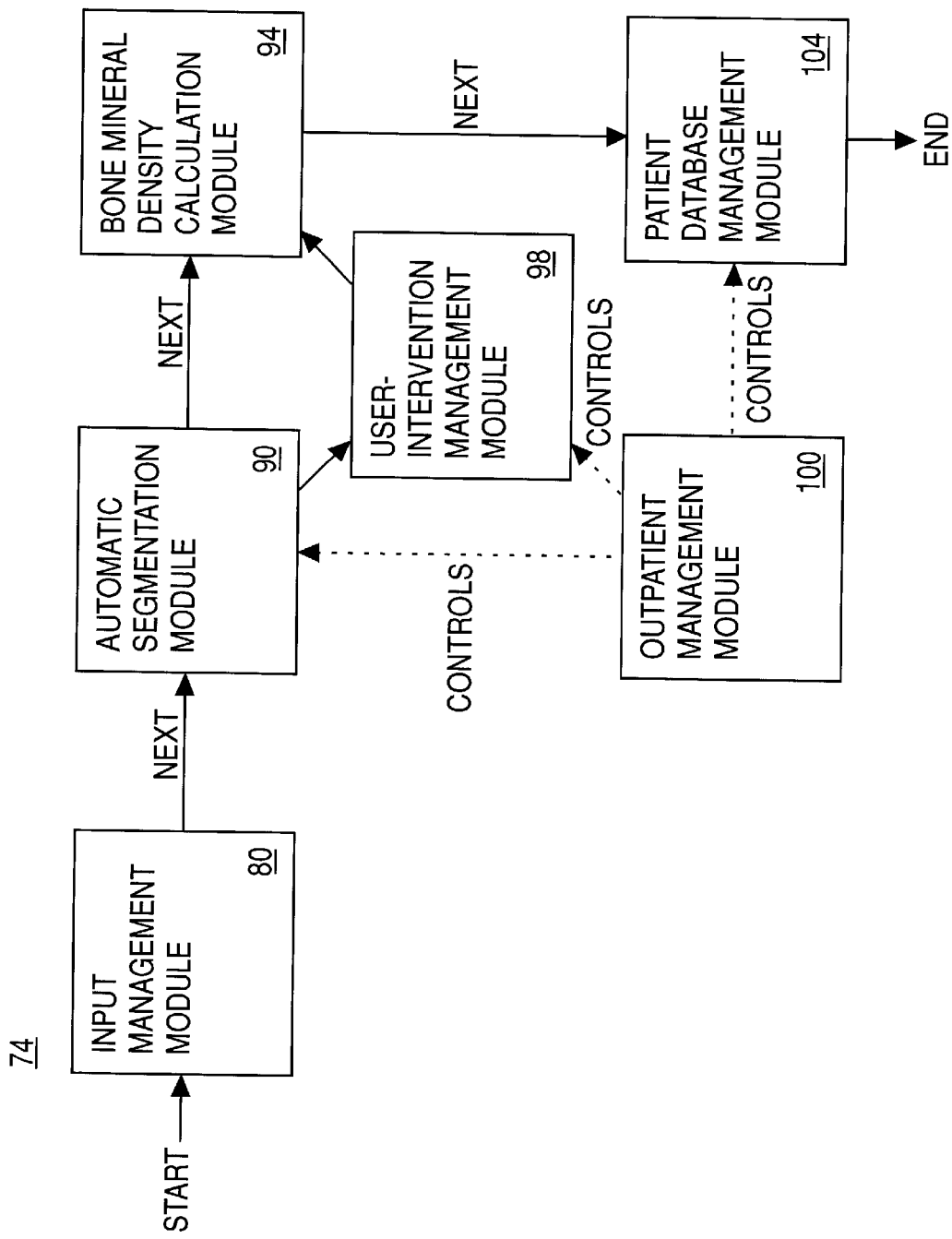
FIG. 5 is a block diagram illustrating one embodiment of the bone mineral density measurement software of FIG. 4.

IMM 80 of FIG. 5 provides an "Acquire from Scanner" option to the user. When selected, BMDMS 74 communicates with the scanner software (e.g., scanner driver) and automatically displays a pop-up screen having the scanner user interface. The scanner user interface can be a window where a user can see the automatically pre-set scanner parameters and settings.

After the scanner is calibrated, a user simply positions the radiograph in the scanner to that elements of interest, such as the aluminum wedge and three middle phalanges, are included in the scan frame. Once the radiograph is properly positioned, a user simply clicks on the "Scan" button, and the radiograph is automatically scanned, and a digital representation of the radiograph is available for use by ASM 90.

The major portions of the invention described below is depicted in block diagram form by FIGS. 5, 6, 7, 9. The input to the system 10 is an x-ray, and the input to the BMDMS 74 is a digital image. The output or end result of the system 10 is a report regarding the bone density of a patient based on the contour, mass and volume corresponding to the and the standard wedge found in that image. An example of the type of image used as input is depicted in FIG. 3.

Bone Mineral Density Measurement Software 74

FIG. 5 is a block diagram illustrating the bone mineral density measurement software (BMDMS) 74 of FIG. 4. Bone mineral density measurement software 74 can include an input management module (IMM) 80 for receiving a digital image from either digitizer 78 or storage 63. BMDMS 74 can also include an automatic segmentation module (ASM) 90 for automatically generating a contour of a predetermined bone. ASM 90 is described in greater detail hereinafter with reference to FIG. 7. BMDMS 74 also includes a bone mineral density calculation module (BMDCM) 94 for receiving the contour from ASM 90 and based thereon for generating a bone mineral density (BMD) result which can be utilized to access a patient's risk of osteoporosis. The BMD result can be a value, such as a BMD index value, and can be used to generate a BMD report.

BMDMS 74 can also include a user intervention management module (UIMM) 98 for allowing a user to provide additional information to fine-tune or otherwise refine the contour provided by ASM 90.

BMDMS 74 can also include an output management module (OMM) 100 for displaying segmentation results, displaying patient data on the screen, or allowing the user to print hard copies of these results.

BMDMS 74 can also include a patient database management module (PDMM) 104 for allowing a user to selectively store patient information and the BMD result in a database, such as a Microsoft Access database available from Microsoft Corporation of Redmond, WA. PDMM 104 allows a health care provider to readily access past BMD results to assess the effectiveness of treatment and also monitor progress or change of a patient's BMD over time.

It is noted that BMDMS 74 and modules 80, 90, 94, 98, 100, and 104 can be stored on a computer readable medium, such as computer readable medium 20 of FIG. 1.

Operation of System 10

Figure 6:
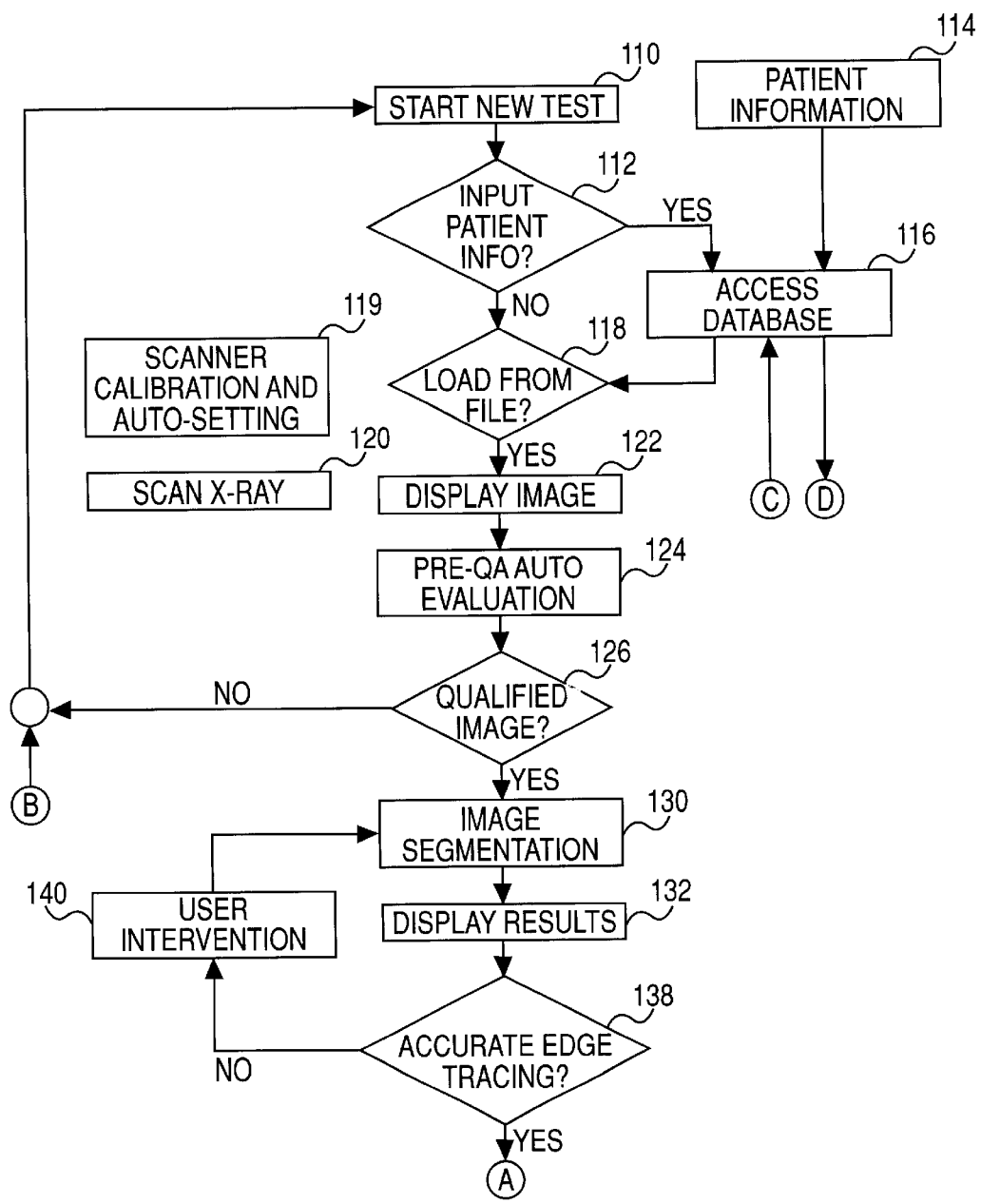
FIG. 6 is a flowchart of the operation of FIG. 4 in accordance with one embodiment of the present invention.
Figure 6:
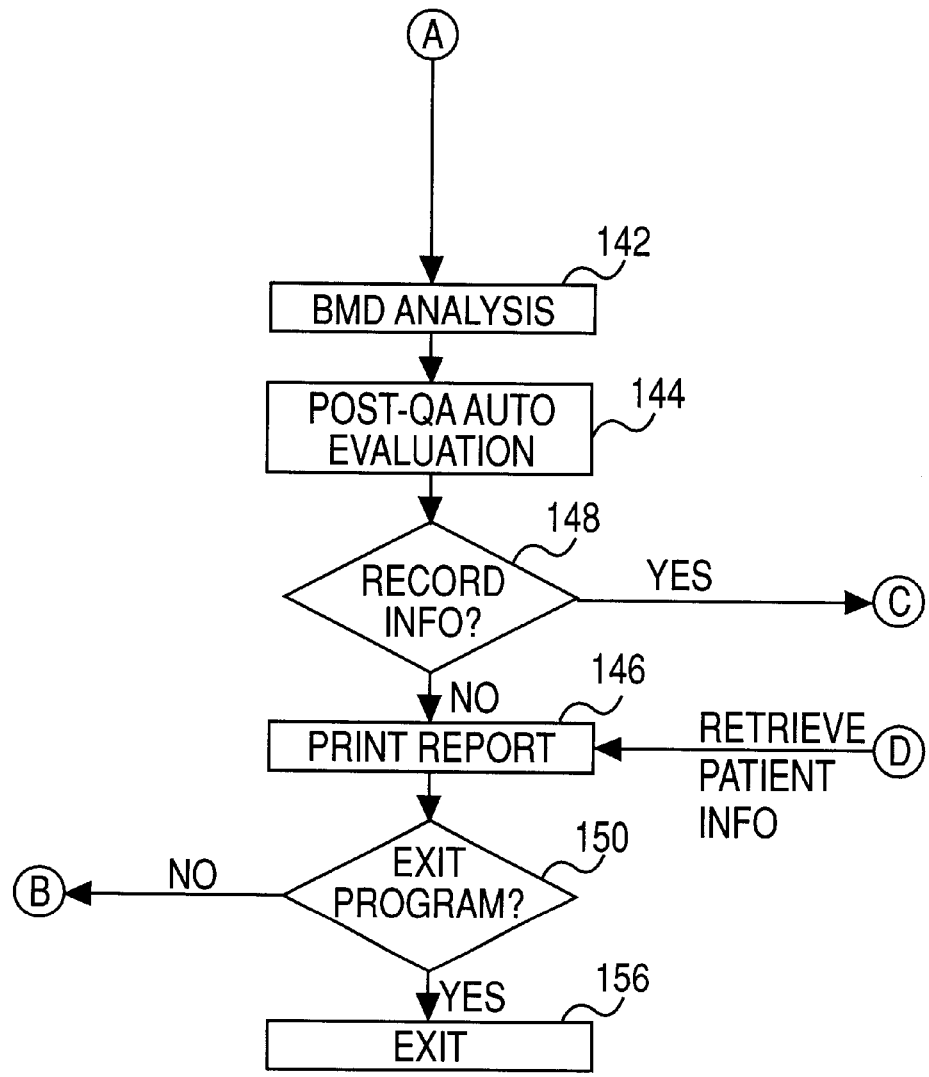

FIG. 6 is a flowchart of the operation of the system 10 of FIG. 1 in accordance with one embodiment of the present invention. In processing step 110, a new test is started by a user. In one example, the present invention provides a "New Test" button that when selected or activated by the user displays a "New Test" pop-up window. The "New Test" pop-up window presents additional preferences or options for selection by the user. In one embodiment, the "New Test" pop-up window has three sections: a first section for allowing a user to select the source of the image to be processed, a second section for allowing a user to select whether one or two exposures are imported at one time, and a third section for allowing the user to input a patient's demographic information into a database.

The first section includes two buttons: a "Load From File" button and an "Acquire From Scanner" button. The second section includes a "One Exposure" preference and a "Two Exposure" preference. The third section includes a Patient Information checkbox for allowing the user to check the box to update the database. These sections are independent in that a user choice in any one section does not affect the selections in the other sections.

In decision block 112, a determination is made whether a user has checked the "Input Patient Information" box. If yes, in step 116, a user can access the database that can be in storage 63 and input a subject's demographic information. For example, a user can input information related to that patient, such as name, address, social security number, birth date, height, weight, x-ray date, age, gender, etc. This information is then associated with the loaded image and can be included in a test report, which is described hereinafter.

If the "Input Patient Information" box is un-checked, processing proceeds to decision block 118. In decision block 118, a determination is made whether the "Load From File" button has been selected. If yes, in processing step 122, (1) the user selects a specific image file, such as a digital radiograph image file, (2) the image file is loaded from storage, such as a hard disk, floppy disk, or other storage media, and (3) the image is displayed on display 66. If no, the "Acquire From Scanner" button has been selected since there are only two possible sources of the image in this example.

In processing step 119, the scanner 18 is calibrated and at least one scanner parameter is automatically set to predetermined values. This step can include the steps of detecting the type of scanner, accessing a look-up table corresponding to the particular type of scanner detected, and automatically setting at least one scanner parameter to a value accessed from the table.

In processing step 120, a radiograph or x-ray film is scanned into PC 14 by utilizing a digitizer 28. After the image is scanned into PC 14, in processing step 122, the image is displayed on display 66. The image can be in one of many different and varying display formats, such as bitmap, gray-scale, TIFF, etc.

When the image is displayed (step 122), an Analyze button is available for activation by the user (i.e., un-grayed). When the Analyze button is clicked, the steps 124–144, which are described in greater detail hereinafter, are carried out by the present invention. Briefly, the present invention automatically segments the middle phalanges of each digit, performs several BMD calculations based on the contours of the middle phalanges, and computes averages of the BMD results from the three digits. The present invention analyzes the image quickly (i.e., in the order of several seconds). A small progress window can optionally be displayed to communicate to the user the name of the detailed task currently being performed. Upon completion, the input image is updated with the edges of the three middle phalanges, the aluminum wedge, and all soft tissue in blue. In addition, the axis of the three digits can also be shown. After the analysis is finished, the "Analyze" button is gray-ed out to indicate that the image processing has been completed.

Specifically, in processing step 124, a pre-quality assurance (QA) is performed. Pre-quality assurance can involve the step of evaluating the optical density (OD) of the background. Due to the uniformity of the X-ray, for example, the pixel values in two regions that are disposed in opposite corners of the image can be averaged to arrive at a representative optical density (OD) for the background of the image. For example, each region can include a plurality of pixels arranged in generally rectangular fashion.

If the optical density (OD) of the background is consistent and in a predetermined acceptable range of values, such as between 0.9 and 1.5, the image is qualified for further processing (i.e., processing proceed to step 130). If the OD of the background is not in the pre-determined acceptable range of values or is not uniform, then the image is rejected and not processed further.

Also, pre-QA can involve the step of determining the noise and contrast level of the image by techniques that are well known in the art. Once the noise level of the image are evaluated, the step of comparing the contrast and noise level of the image to predetermined threshold values can be performed. If the contrast of the image is out of the predetermined contrast threshold range or the noise level of the image exceeds a predetermined noise threshold, the image is also rejected and not processed further (i.e., processing proceed to step 110). Optionally, a message can be displayed to the user to inform the user that the image has been rejected for quality reasons.

The qualified image is then provided to automatic segmentation module 90, and processing continues at processing step 130. In processing step 130, automatic segmentation module 90 receives the qualified image file and automatically segments the middle phalange. Segmentation involves generating the contours of the middle phalange (i.e., the coordinates of the boundary of the middle phalange). In processing step 132, the results of the segmentation are displayed on the display 66. In one embodiment, the finger, bone, and wedge contours are shown in a blue color to easily differentiate the edges from the digital image that includes 256 gray shades.

In processing step 138, a determination is made whether the segmentation result as shown on display 66 is acceptable to a user. If yes, processing continues to processing step 142. If no, in processing step 140, a user can be prompted to provide information that is utilized to refine the segmentation. For example, user intervention can include the provision of two points: (1) one point on the top segment of the joint space, and (2) one point on the bottom segment of the joint space.

After user intervention, the present invention re-segments (step 130) the middle phalange and displays (step 132) the new contour on the display 66 for viewing by the user. Processing steps 130, 132, 138 and 140 can be continued until the user is satisfied with the segmentation as shown on the display 66.

In processing step 142, the bone mineral density (BMD) is calculated by utilizing the contour of the middle phalange provided by ASM 90.

In one embodiment, the radiograph includes a two exposures: exposure A and exposure B. Both X-rays include three fingers of interest and the wedge although the X-rays have been taken under different light conditions. When the X-ray is scanned into the system, there are two image files created and resident in random access memory.

When executing the program of the present invention, both image exposures are loaded and processed. The user works with each image until satisfied with the results. The program then performs the post-QA described above, and if the bone densities calculated for the exposure A and exposure B pass the post-QA tests, the density of all six middle phalanges are averages to determine the bone density index. This bone density index, along with other associated information, is then provided in the report to the user or saved to the database.

In processing step 144, OMM 100 automatically performs post-quality assurance (post-QA) on the bone density measurements. In this embodiment, the present invention calculates the bone density for middle phalange one (MP1), middle phalange two (MP2), and middle phalange three (MP3) for both exposure A and B. Post-QA can involve comparing the difference of bone density among the three phalanges in the same exposure or the same phalange between two exposures. If the bone densities between the middle phalanges vary by more than a predetermined percentage, such as 2%, the bone density results are rejected and not provided to the user. A variation between bone densities of the middle phalanges indicates that there is an operator error either in the scanning process, user intervention or the X-ray process. A message can be displayed to the user regarding the inconsistent results and ask the user to rescan or re-take the X-ray.

In processing step 146, the BMD report is printed. Once the analysis is complete, a user can select a "Report" button in order to generate a BMD report. When the "Report" button is activated, a pop-up print preview window is displayed for viewing by the user. If the user had previously inputted patient information in step 112, this information is retrieved from the database and reflected in the report. If the user is satisfied with the information in the report, the user selects a "Print" command from the "Report" pull-down menu to start the printing process.

FIG. 18 illustrates an exemplary report that can be generated by the system of the present invention. The BMD report can have different information fields and formats. In one embodiment, the BMD report includes (1) a highlighted box that provides a "Skeletal Status" and a T-Score; (2) a numerical display of the BMD index and the T-Score values; and (3) a graph of the T-Score value as a function of the age of age of subjects. The skeletal status can be one of the following: normal, low bone mass (Osteopenia), or Osteoporosis. The T-Score is a clinical result that reflects the number of standard deviations the patient's value is above (+) or below (-) the reference mean bone mass for young adult normal values. The BMD index is the average bone mineral density of the middle phalanges and is expressed in arbitrary units that reflect the dimensions of mass per unit volume. The BMD index is utilized to calculate the T-Score that depends on factors such as gender and race. A skeletal status graph of the T-Score versus the age of the subjects is provided for use in physician prognosis.

In processing step 148, a determination is made as to whether a user has chosen to record the analysis and report in a patient database by selecting a "Save Report" button. If yes, in processing step 154, the analysis and report are saved in a patient database, and processing proceeds to decision block 150. If no, processing is complete for the current image, and processing proceeds to decision block 150.

Decision block 150 determines if the user has chosen to exit the program by selecting an "Exit" command from a "File" pull-down menu. If yes, in processing step 156, an exit from the program is performed. If no, processing proceeds to step 110 to start a new test.

Figure 7:
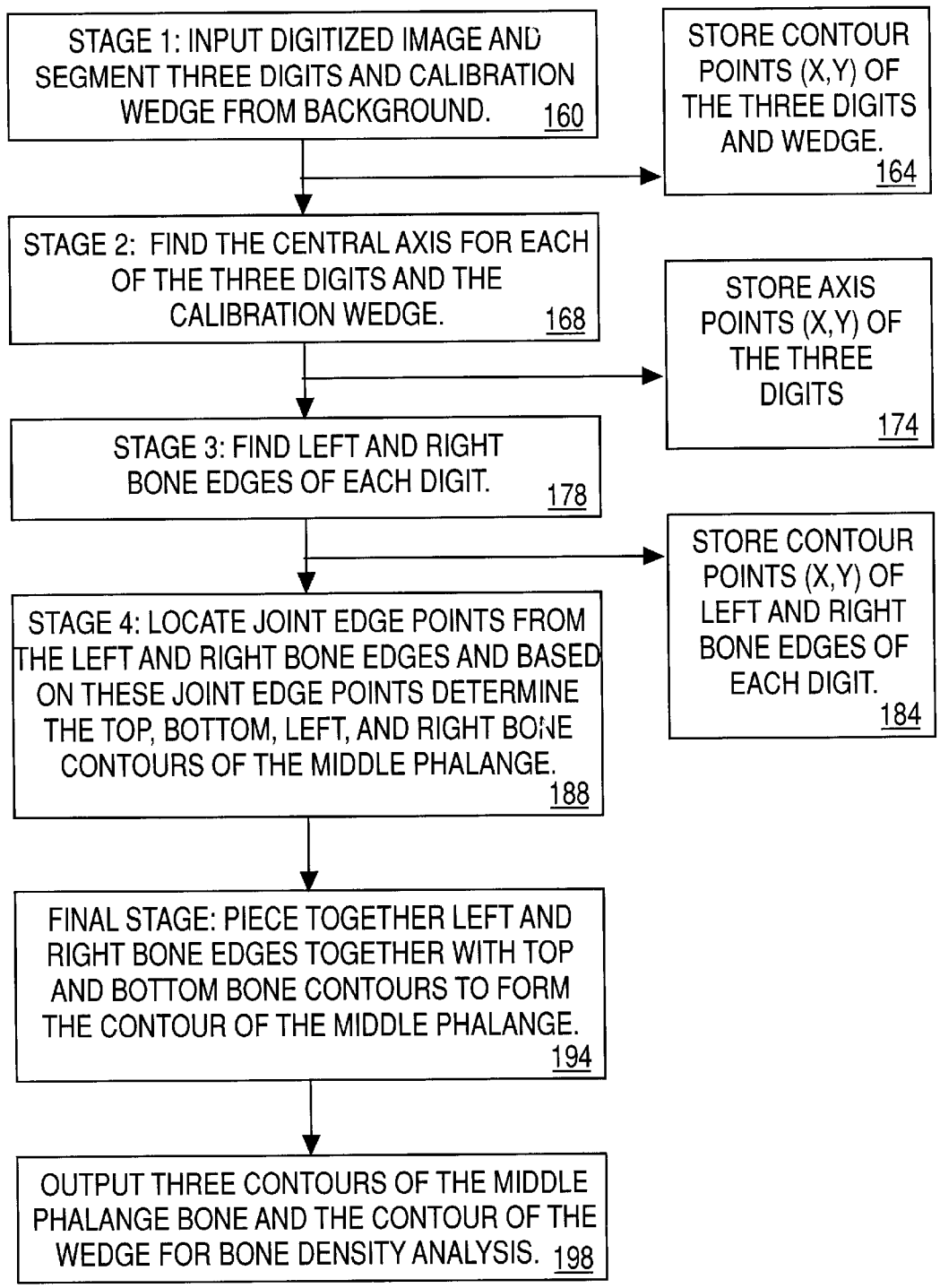
FIG. 7 is a flowchart illustrating in greater detail the step of automatically segmenting the middle phalange of FIG. 6.

FIG. 7 is a flowchart illustrating in greater detail the step of segmenting (step 130) the middle phalange automatically of FIG. 6. The processing is divided into five stages (steps 160, 168,178, 188, and 194 in FIG. 7) where each stage is focused on a target object. Accordingly, the present invention has the advantage of having flexibility, scalability, and interoperability. Each stage can be written as a self contained module in an object-oriented fashion so that the interface between the stages is constant even when the methods implemented by a stage are different, updated or otherwise improved (i.e., a change in the method of any of the stages does not disrupt the flow or operation of the present invention or require re-programming of the entire program, but only the affected module).

In processing step 160 (i.e., the first stage), the three digits and the calibration wedge are segmented from the background. In processing step 164, the contour points (x,y) of the three digits and wedge are stored. In processing step 168 (i.e., the second stage), the central axis of each of the three digits is determined. In processing step 174, the axis points (x,y) of the three digits are stored. In processing step 178

(i.e., the third stage), the left bone edge and the right bone edge of each digit are determined. In processing step 184, the contour points (x,y) of the left and right bone edges of each digit are stored.

In processing step 188 (i.e., the fourth stage), the joint edge points are located from the left and right bone edges. Based on these joint edge points, the top contour, bottom contour, left contour, and right contour of the target bone (e.g., the middle phalange) is determined. In processing step 194 (i.e., the fifth stage), the left and right bone edges are pieced together with the top and bottom joint space contours to form the contour of the middle phalange. In processing step 198, the three contours of the middle phalange bone and the contour of the wedge are provided for bone density analysis.

Further details concerning particular embodiments of the automatic segmentation module of present invention may also be found in the co-pending patent application, entitled "Method For Automatically Generating A Contour Of A Target Bone Based From A Digital Image" by inventors Brent J. Liu, Hyeonjoon Shim, David Edelstein, Eric Duff, and Xiaoli Bi, which is filed concurrently herewith and which is incorporated herein by reference.

Bone Mineral Density Analysis

Figure 9:
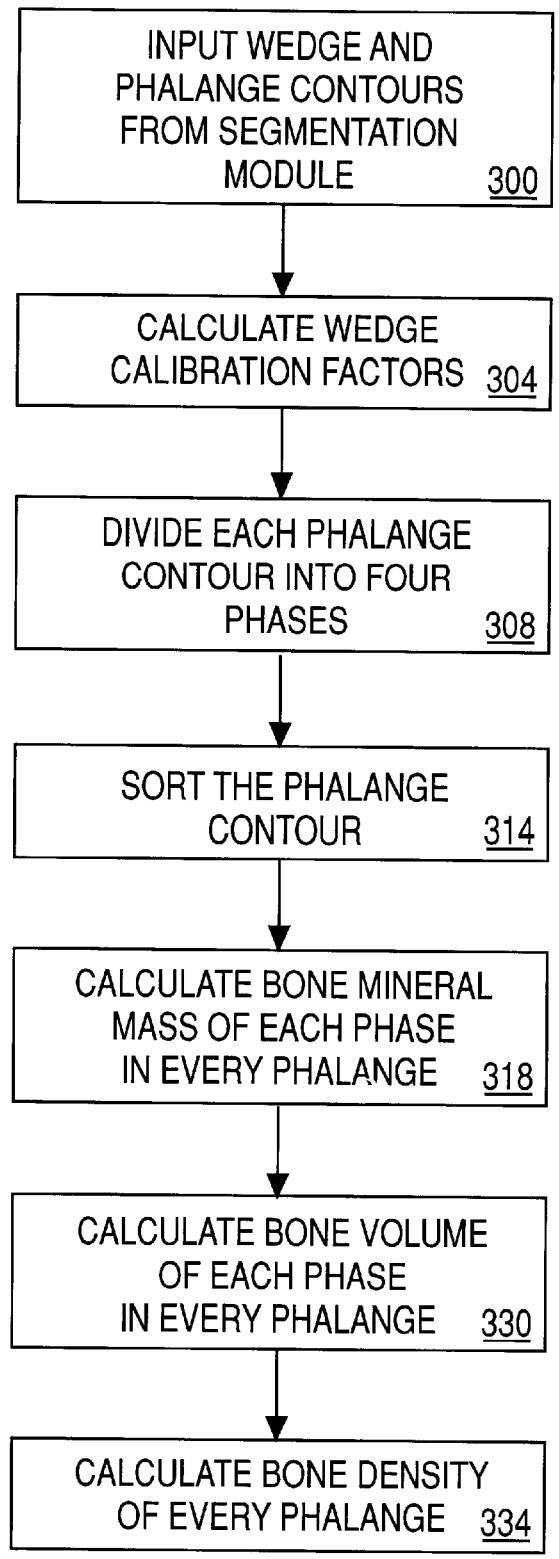
FIG. 9 is a flow chart illustrating in greater detail the step of performing the BMD analysis of FIG. 6 according to one embodiment of the present invention.

FIG. 9 is a flow chart illustrating in greater detail step 142 of FIG. 6 where the present invention performs the BMD analysis. In the preferred embodiment, BMDCM 94 utilizes the following steps to determine the bone density of the bone. In step 300, bone mineral density calculation module (BMDCM) 94 receives the wedge contour and bone contour (e.g., the phalange contours) from ASM 90 after the processing steps illustrated in FIG. 7. In step 304, BMDCM 94 determines a calibration factor based on known wedge data and the observed optical density of selected pixel values of the wedge. The calibration factor is calculated utilizing methods that are known by those of ordinary skill in the art. This calibration factor can be used to generate uniform results that are independent of a particular radiograph machine or one type of radiograph film. For example, the calibration factor can compensate for differences between radiograph machines and types of radiograph film.

Figure 8:
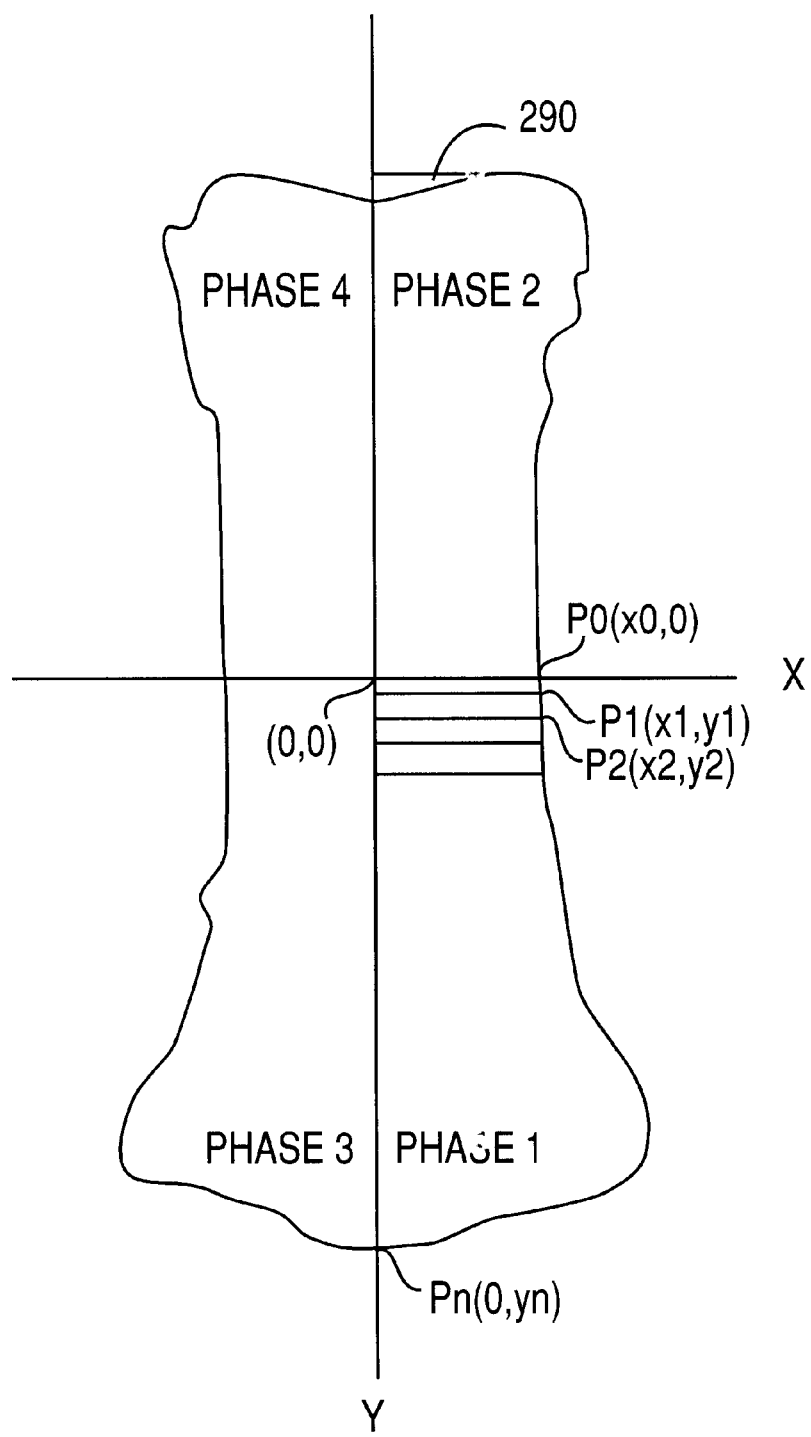
FIG. 8 illustrates a target bone and a method utilized by one embodiment of the present invention to determine the bone density of target bone based on the contour of the target bone.

In step 308, BMDCM 94 divides the contour into four phases as illustrated in FIG. 8. In step 314, each phase of the contour is sorted in curve order by utilizing a sort algorithm, such as a minimum tree algorithm, which is well known in the art. In step 318, the bone mass of each phase is then determined pixel-by-pixel, and the overall mass of the bone is calculated by adding all the pixels of the bone. In step 330, the volume of the bone in each phase is calculated. In processing step 334, BMDCM 94 calculates the bone density by dividing the bone mass by the bone volume for each phalange. Each of these steps are described in greater detail hereinafter.

Bone Mass Calculation (Step 318)

FIG. 8 illustrates an exemplary bone and the technique utilized by the present invention to calculate the mass of the bone. In this example, the bone is a middle phalange, and FIG. 8 shows the contour of the middle phalange that is divided into four phases. The bone mass for each phase is first calculated, and then the results of each phase is summed to determine the total mass of the bone.

For each phase, every pixel inside the bone contour is calculated and the total bone mineral mass is the summation of all the pixels. For example, calculation and summation of the bone mineral mass starts at a current point on the contour and proceeds horizontally pixel-by-pixel toward the y-axis until the y-axis is reached. Then, the process continues at the next point on the contour and proceeds horizontally pixel-by-pixel toward the y-axis until the y-axis is reached. This process is repeated until all the points on the contour have been processed, and all pixels inside the bone contour have been calculated.

For example, for phase 1, the starting point is the first contour point $P_1(x_1,y_1)$. The first row to be processed extends from the first contour point $P_1(x_1,y_1)$ to $(0,y_1)$. This row is referred to herein as the first element. Then, the second row or element to be processed extends from the second contour point $P_2(x_2,y_2)$ to $(0,y_2)$. This procedure proceeds row-by-row or element-by-element until the last contour point for the current phase $P_n(0,y_n)$ is encountered. When the last element of the current phase is reached, the mass for that phase has been determined.

Specifically, the following is an expression utilized by BMDCM 94 for determining the pixel bone mass:

$$\text{Pixel Bone Mass} = A*(ST\_OD - BGRD\_OD)/(B\_OD - BGRD\_OD)$$

where ST_OD is the soft tissue optical density adjacent to the bone contour at a y value identical to the y value of that row or element; BGRD_OD is the background optical density of the image; and B_OD is the bone optical density measured at each pixel inside the bone.

The following expressions are utilized by BMDCM 94 for determining the total bone mass:

$$\text{Total Bone Mass} = \text{SUM}\,[(Y_n - Y_{n-1})*\text{Pixel Bone Mass}]\,(\text{for phase 1 or phase 3, where } y>0) \text{ or}$$

$$\text{Total Bone Mass} = \text{SUM}\,[(Y_n - Y_{n+1})*\text{Pixel Bone Mass}]\,(\text{for phase 2 or phase 4, where } y<0).$$

The other phases are then processed in sequential phase order in the same manner.

One novel aspect of this approach to determine bone mass is that the pixel values attributable to soft tissue (e.g., the shadowed portion 290 in phase 2) are subtracted from the total mass since the shadowed portion represents soft tissue and not bone. The shadowed portion is determined by the predetermined condition. The predetermined condition can be a determination whether $Y_n - Y_{n-1}$ is less than zero, where $Y_n$ is the y-value for the current contour point, and $Y_{n-1}$ is the y-value for the previous contour point. In other words, this condition detects those points that are attributable to soft tissue and automatically subtracts these pixel values from the total bone mass value. The predetermined condition for adjusting the bone mass is dependent on the particular phase, which corresponds to the shape of the bone edge in that particular phase.

Whereas prior art approaches ignored a portion of the trabecular bone in order not to include unwanted soft tissue pixels, the present invention provides a novel compensation mechanism to account for the entire trabecular bone without sacrificing accuracy. Since osteoporosis begins in the trabecular bone and moves to the cortical bone, the prior art lost important information by ignoring a portion of the trabecular bone. This important information is captured by the present invention without injecting error by including pixels in soft tissue.

Bone Volume Calculation (Step 330)

FIG. X illustrates how the bone volume is calculated for phase one. The bone is estimated to be a plurality of cylinders that are stacked upon each other where the cylinders can have different radii. The volume of each of these cylinders is calculated individually, and the results summed to determine the bone volume for a particular phase. In order to calculate the total bone volume, the present invention adds the volume for each phase.

For example, the following approach can be utilized to determine the bone volume for the first phase. For each point (P(x,y)) on the contour, the radius is assigned the value of x (e.g., the radius corresponding to $P_1$ is $x_1$, and the radius corresponding to $P_2$ is $x_2$). The height (h) is simply the y value of the current contour point minus the y-value of the previous contour point (e.g., for $P_2$, the height is equal to $y_2-y_1$). The volume for each cylinder is calculated by the formula: $V=(\pi(r)^2*h)/2$, where r is the radius of each circular slice, and h is the height of the cylinder. Accordingly, the volume of the bone for a particular phase can be accumulated as the point moves along the contour for that phase.

For example, phase one begins at P(x,0) and ends at P(0,y)). Phase two begins at P(x,0) and ends at P(0,-y)). At $P_m$, the y value of the point on the contour reaches a maximum for the current phase. Accordingly, the volume that is calculated for every point (e.g., $P_c$) on the contour after $P_m$, is subtracted from the accumulated total (i.e., the running total). This subtraction compensates for those points (e.g., $P_b$) on the contour where a portion (e.g., portion 280) of the pre-calculated volume included the volume of soft tissue in addition to the volume of the bone.

Graphical User Interfaces

Figure 10:
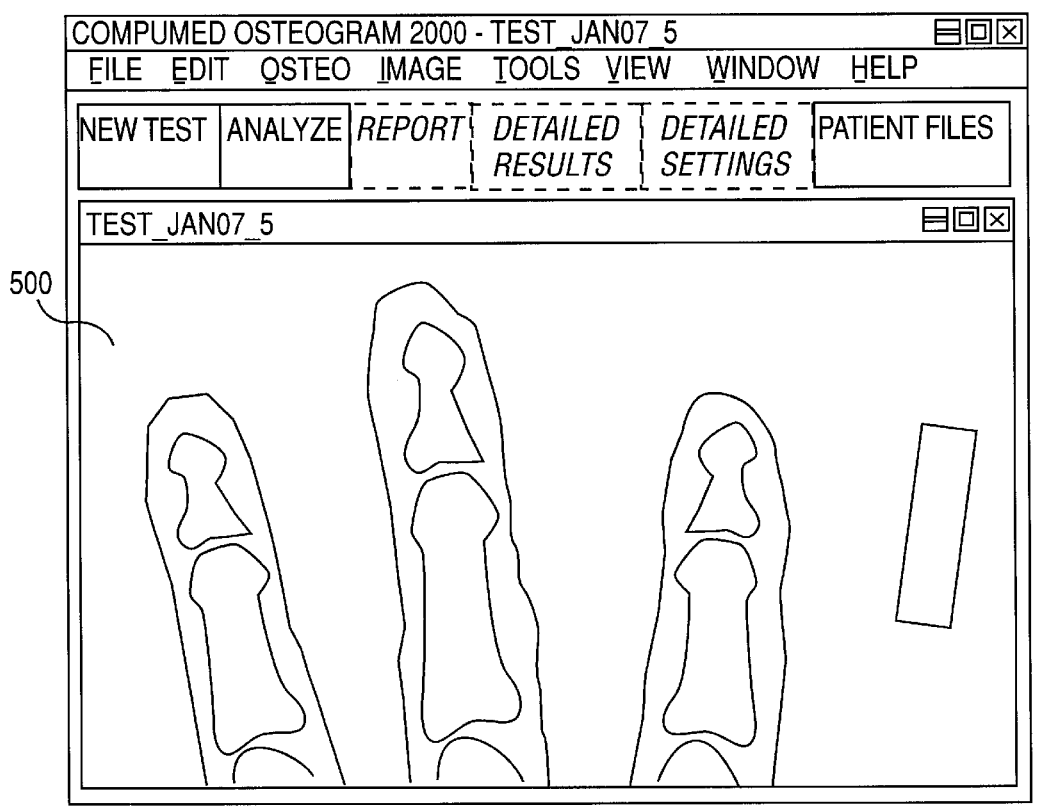
FIG. 10 illustrates a display window of an imported image prior to processing by the bone mineral density measurement software of the present invention.

FIG. 10 illustrates a display window 500 of an imported image of a selected region of interest determined previously by a user through the driver software of the scanner 18. The imported image includes the three digits of a patient's hand and the calibration wedge before any processing by the bone mineral density measurement software of the present invention.

Figure 11:
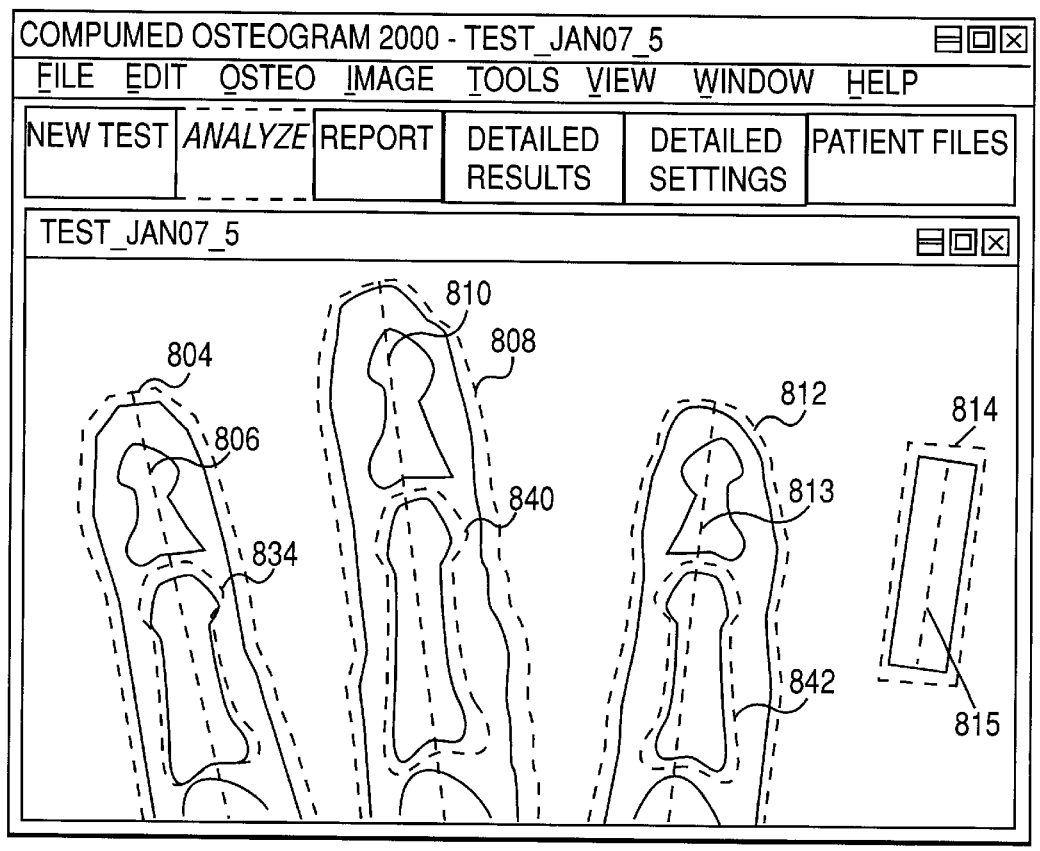
FIG. 11 illustrates an display window of the image that includes the contours of the three digits, middle phalange in each digit, and the calibration wedge after processing by the bone mineral density measurement software of the present invention.

FIG. 11 illustrates an display window of the image after processing the present invention. The BMDMS 74 of the present invention receives the imported image of FIG. 10 as input and automatically generates the contours of the three digits of a patient's hand, the middle phalanges of each digit, and the calibration wedge. These contours can be displayed as illustrated in FIG. 11. One novel aspect of the present invention is that the contours of the fingers, middle phalanges, and the wedge are automatically extracted from the image and automatically displayed for viewing by the user.

The screen includes a plurality of pull-down menus 800. Each pull-down menu, when activated by the user, reveals additional preferences or commands for selection by user.

The screen also includes function buttons 802 across the top of the window. These buttons 802 are provided by the present invention to allow a user to select a particular feature or command provided by the program. The screen shows the contours 804, 808, 812 of the fingers, the middle axis 806, 810, 813, corresponding thereto, the contour of the middle phalanges 834, 840, 842, the contour of the wedge 814, and the middle axis 815 of the wedge. These features are calculated automatically and displayed automatically for viewing by the user. In one embodiment, these features are highlighted in a color (e.g., blue) that is different from the background.

Figures 12, 13, 14:
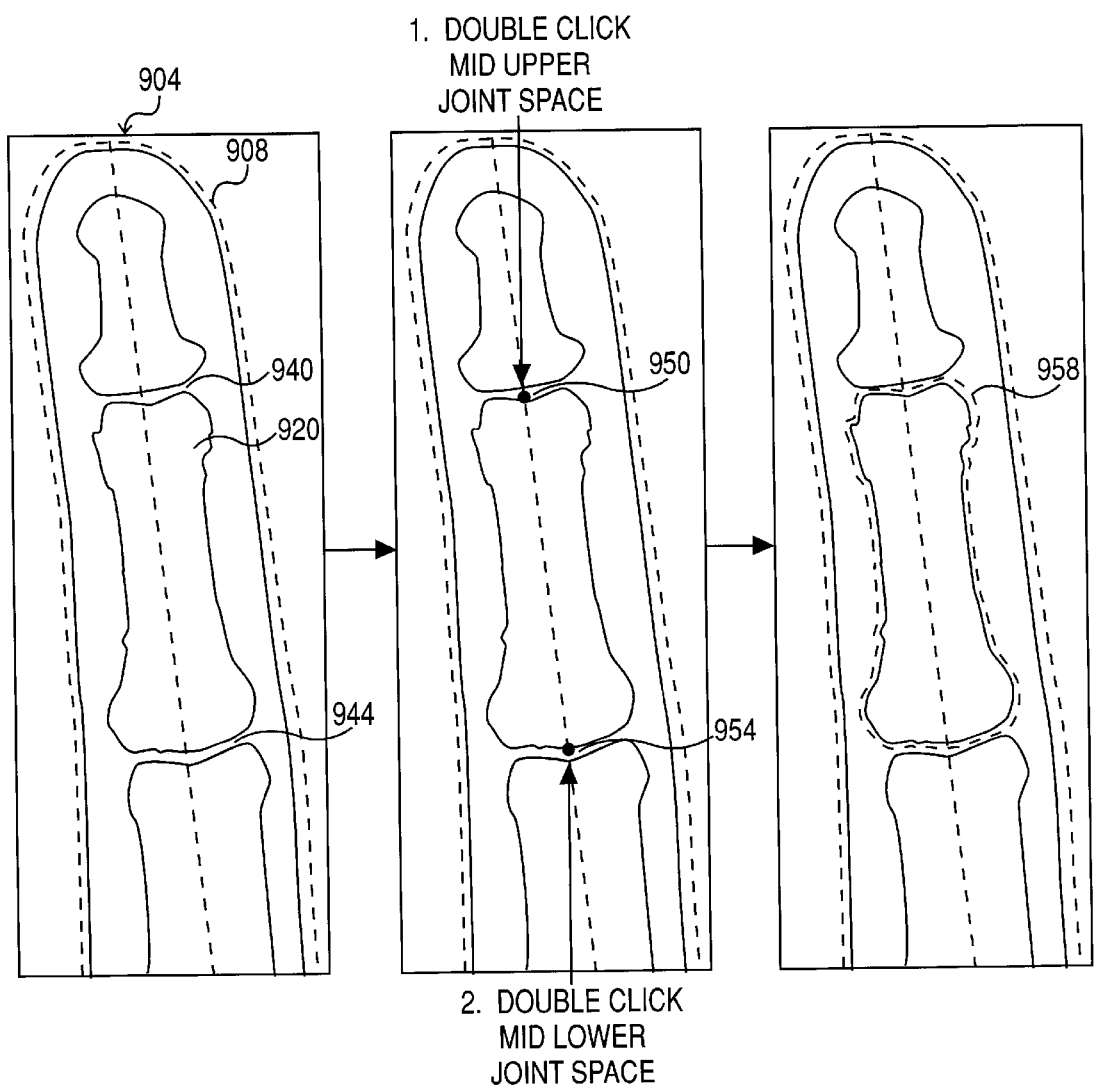
FIG. 12 illustrates a first graphical user interface window according to one embodiment of the present invention.
FIG. 13 illustrates how a user can employ the first graphical user interface window of FIG. 12 to provide input according to one embodiment of the present invention.
FIG. 14 illustrates a contour of the middle phalange that is generated based on the user input of FIG. 13.

FIGS. 12–14 illustrate a first graphical user interface window 900 showing the contours of the phalanges generated automatically by the bone mineral density measurement software of the present invention and providing an opportunity for a user to provide refinement input. This first GUI is also referred to herein as the "Click Top, Click Bottom" GUI. A digit 904 includes a digit contour 908 and phalange 914. Phalange 914 includes a distal phalange, middle phalange 920 (which in this case is the target bone or the "bone of interest"), and proximal phalange. Middle phalange 920 is separated from the distal and proximal phalanges by a top joint space 940 and a bottom joint space 944.

FIG. 13 illustrates how the GUI of the present invention allows a user to specify two points: the top joint space point (e.g., point 950) and the bottom joint space point (e.g., point 954) which define the upper and lower boundaries of the middle phalange 920. A user can position a cursor in the joint areas to click and specify a top joint space point and a lower joint space point anywhere in those areas. The program of the present invention receives these two points and automatically calculates the contour for middle phalange 920 and automatically displays the contour on the screen. FIG. 14 illustrates the bone contour 958 based on the user input. The user can repeat this step until the user is satisfied with the displayed contour of the middle phalange. For example, when the user clicks on a new top joint space point and a new bottom joint space point, the present invention receives these two points and automatically re-calculates the contour for middle phalange 920 and automatically displays the revised contour on the screen.

The present invention also provides a "Build-from-Raw" GUI that allows a user to click a top joint point and a bottom joint point. Based on these two points the present invention automatically calculates and displays the contour for the target bone. This GUI is especially useful when the bones are fused or otherwise do not have a well defined joint space.

Figure 15:
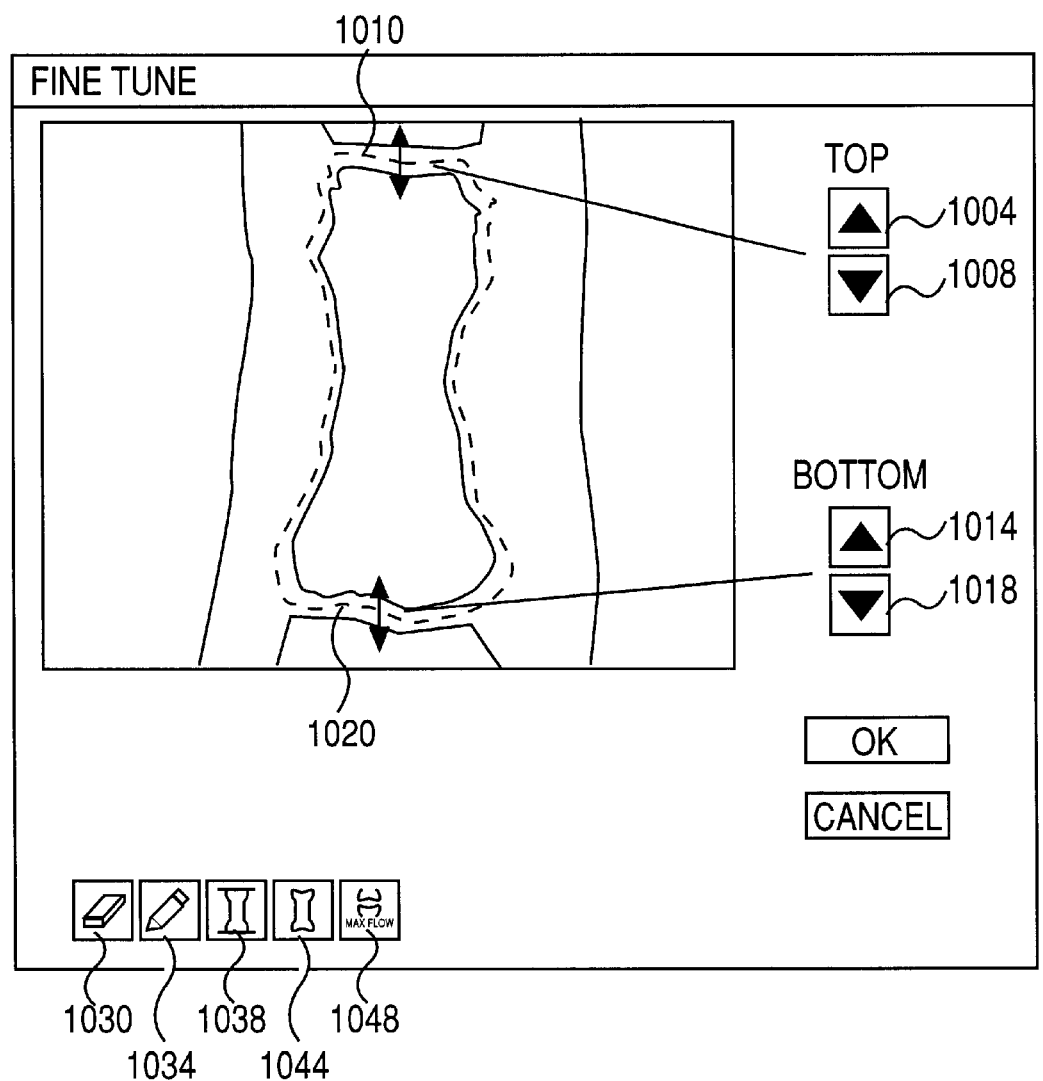
FIG. 15 illustrates a second graphical user interface window that allows the user to input information according to one embodiment of the present invention.
Figure 16:
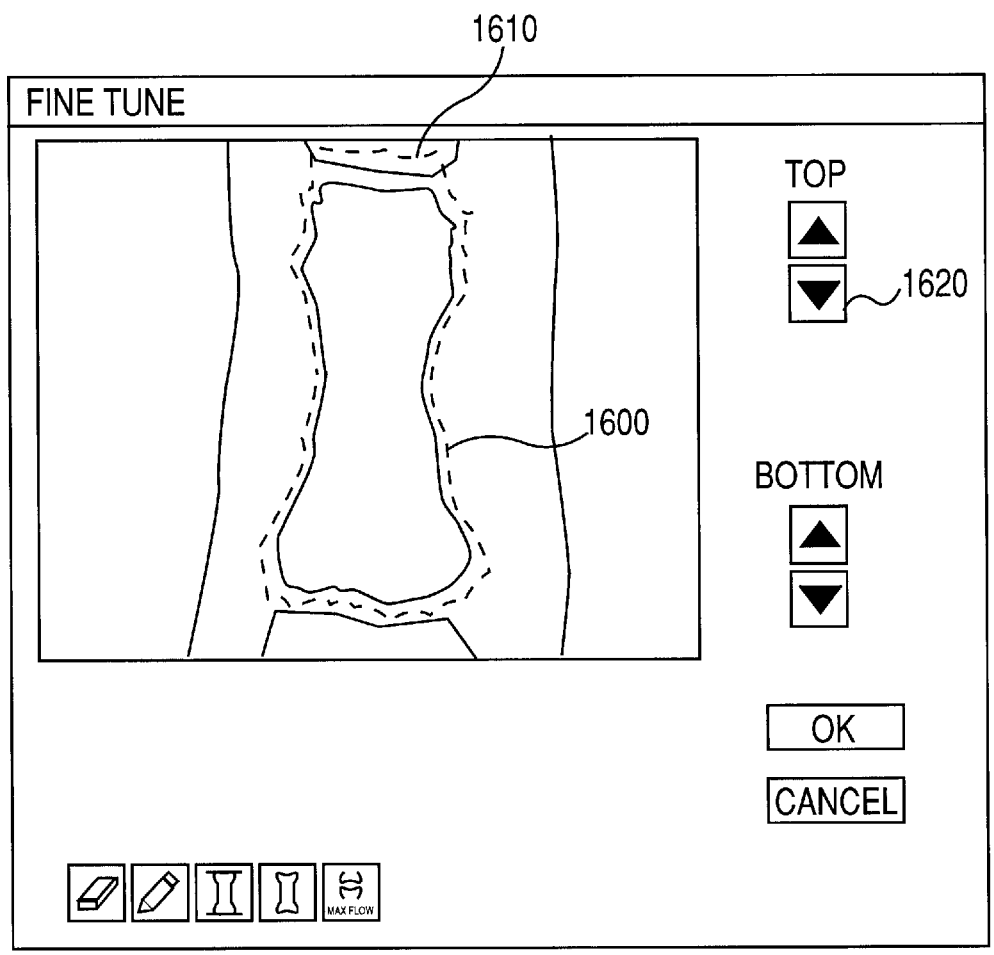
FIG. 16 illustrates a bone contour that has a top edge requiring refinement and how the second graphical user interface window of FIG. 15 can be used to provide input to the bone mineral density measurement software of the present invention.
Figure 17:
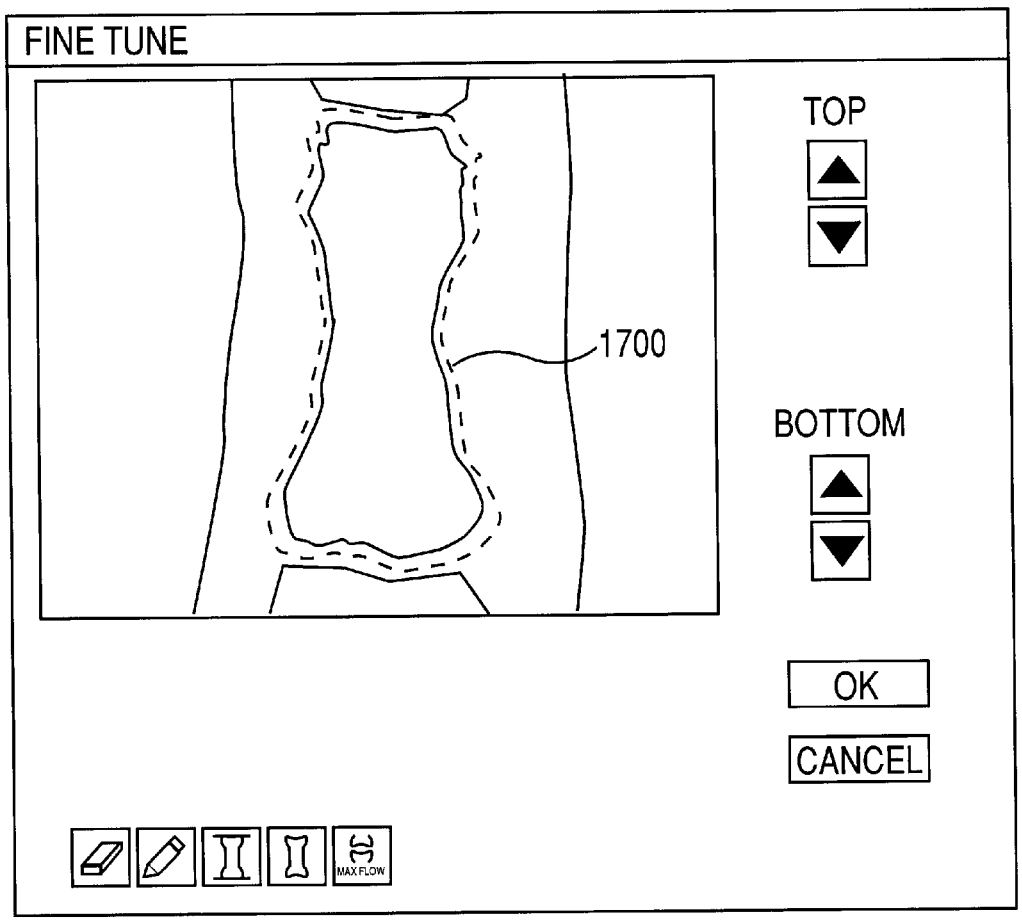
FIG. 17 illustrates the dynamically revised and re-displayed bone contour based on the input provided by the user in FIG. 15.

FIGS. 15–17 illustrate a second graphical user interface window 1000 that allows the user to input further information. Once the "Click Top/Bottom GUI has been selected, a user can open a "Fine Tune" window to selectively move (either up or down) the top or bottom joint points on a pixel by pixel basis. GUI 1000 is referred to as the "Fine Tune" GUI. GUI 1000 includes an up arrow button 1004 and a down arrow button 1008 for the top bone edge 1010, and an up arrow button 1014 and a down arrow button 1018 for the bottom bone edge 1020. When the user selects one of these buttons, a revised joint point is provided to the program of the present invention, which in turn automatically re-calculates the bone contour based on the input.

Moreover, the joint point can be incremented or de-cremented along the medial axis, as the case may be, on a pixel by pixel basis, and the revised contour (e.g., contour 1600) is automatically re-calculated and displayed for the user as illustrated in FIGS. 16 and 17. Specifically, FIG. 16 illustrates a bone contour (e.g., contour 1600) that has a top edge 1610 requiring refinement and how the second graphical user interface window of FIG. 15 can be used to provide input to the bone mineral density measurement software of the present invention. FIG. 17 illustrates the dynamically revised and re-displayed bone contour 1700 based on the input (e.g, 1620) provided by the user in FIG. 15.

GUI 1000 also includes an eraser tool 1030 for erasing only the bone contour, as displayed, without affecting the remainder of the image, a pencil tool 1034 for selectively drawing the contour, a flat edge button 1038 for fused bones, a curved edge button 1044 for arthritic bones, and a maximum flow button 1048 for normal bones. The flat edge button 1038 causes ASM 90 to estimate the top and bottom bone contours as a straight line. The curved edge button 1044 causes ASM 90 to generate the top and bottom bone contours as a predetermined curved edge. The maximum flow button 1048 causes ASM 90 to execute a pre-defined maximum flow algorithm for determining the contour of the top and bottom edges.

The foregoing description has provided numerous examples of the present invention. It will be appreciated that various modifications and changes may be made thereto without departing from the broader spirit and scope of the invention as set forth in the appended claims.

What is claimed is:

1. In a system having a personal computer (PC) for executing programs and a scanner coupled to the PC for scanning images, a method for computing a bone mineral density value based on a digital image comprising the steps of:
   a) configuring the scanner to scan radiographs and to generate digital images based on the radiographs; wherein the digital images are qualified for radiographic absorptiometry bone density analysis;
   b) scanning a radiograph by utilizing the configured scanner to generate a qualified digital image; and
   c) automatically generating a bone mineral density value based on the qualified digital image.

2. The method for computing a bone mineral density value of claim 1 wherein the system further includes scanner control software for controlling the scanner, the scanner control software having a plurality of configurable scanner parameters; and wherein the step of configuring the scanner to scan radiographs and to generate qualified digital images based on the radiographs includes setting at least one scanner parameter to a pre-defined value.

3. The method for computing bone mineral density value of claim 2 wherein the step of setting at least one scanner parameter to a pre-defined value includes:
   a) setting the dimensions of the image to predetermined image dimensions;
   b) setting the dimensions of the pixels to a predetermined pixel dimension;
   c) setting the image type to a predetermined image type;
   d) setting the dynamic range of gray-scale to a predetermined dynamic range; and
   e) setting the gray-scale response to a predetermined gray-scale response.

4. The method for computing bone mineral density of claim 3
   wherein the step of setting the dimensions of the image to predetermined image dimensions includes the step of setting the dimensions of the image to the dimensions of 1024 pixels by 600 pixels;
   wherein the step of setting the dimensions of the pixels to a predetermined pixel dimension includes the step of setting the dimension of each pixel to a value in the range of 104 microns to 116 microns;
   wherein the step of setting the image type to a predetermined image type includes the step of setting the image type to gray-scale;
   wherein the step of setting the dynamic range of gray-scale to a predetermined dynamic range includes the step of setting the dynamic range of gray-scale to 12 bits; and
   wherein each scanner type has a corresponding pre-defined look-up table that specifies at least one scanner setting for affecting the gray-scale response; wherein the step of setting the gray-scale response includes determining the type of scanner and accessing a corresponding look-up table based on the scanner type, and setting at least one scanner setting to a value specified by the predetermined look-up table.

5. The method for computing bone mineral density of claim 4 wherein setting at least one scanner setting to a value specified by the predetermined look-up table includes setting one of the brightness to zero, the contrast to zero, the shadow to zero, the highlight to a value in the range of 200 to 256, the midtone to a value in the range of 1.4 to 1.6, and the gamma to a value in the range of 0.8 to 1.6.

6. The method for computing a bone mineral density value of claim 1 wherein the system further includes scanner control software for controlling the scanner, the scanner control software having a plurality of configurable scanner parameters; and wherein the step of configuring the scanner to scan radiographs and to generate qualified digital images based on the radiographs includes automatically determining the type of scanner coupled to the PC; and
   automatically setting at least one scanner parameter in the scanner control software to a pre-defined value based on the scanner type.

7. An apparatus for determining bone density comprising:
   a scanner for scanning a radiograph and generating a digital image based on the radiograph, said digital image having at least one digit, said digit having a target bone, and a calibration wedge;
   a personal computer (PC) coupled to the scanner for receiving the digital image and for executing programs; and
   a bone analysis program when executing on the PC for receiving the digital image, automatically generating a digit contour, a calibration wedge contour, and a target bone contour from the digital image, and automatically displaying the digit contour, the contour of the calibration wedge, and the contour of the target bone for display.

8. The apparatus for determining bone density of claim 7 further comprising:
   a monitor coupled to the PC for displaying the digit contour, the contour of the calibration wedge, and the contour of the target bone for display.

9. The apparatus for determining bone density of claim 7 wherein the bone analysis program generates a bone mineral density result based on the contour of the target bone, said apparatus further comprising:
   a printer coupled to the PC for printing the bone mineral density result.

10. An apparatus for determining bone density comprising:
    an x-ray source for generating x-rays;
    a digital panel having an array of x-ray detectors for receiving the x-rays and generating a digital image of an object being imaged, said digital imagehaving a digit with a target bone and a calibration wedge;
    a processor coupled to the scanner for receiving the digital image and for executing programs; and
    a bone analysis program when executing on the processor for receiving the digital image, automatically extracting a digit contour, a calibration wedge contour, and a target bone contour from the digital image, and automatically displaying the digit contour, the contour of the calibration wedge, and the contour of the target bone.

11. The apparatus of claim 7 further comprising
    a first graphical user interface for receiving user input to refine the contour of the target bone and for dynamically re-calculating and re-displaying a new contour for the target bone based on the user input.

12. The apparatus of claim 7 further comprising
    a second graphical user interface for displaying a pop-up window upon selection by user, providing an upbutton and a down button for each bone edge, and dynamically re-calculating and re-displaying a new contour for the target bone based on the user input.

13. The apparatus of claim 7 further comprising an automatic bone extraction module for automatically extracting the contour of a target bone; and a bone mineral density module for receiving the contour of the target bone and, based thereon, for calculating a bone mineral density based on the contour of the target bone.

14. A method of determining a bone density measurement comprising:

receiving an image having a target bone;

automatically calculating a contour of the target bone from the image; and displaying the contour of the target bone.

15. The method of claim 14 further comprising:

receiving user input;

based on the user input, automatically re-calculating the contour of the target bone; and re-displaying the re-calculated contour of the target bone.

16. The method of claim 15 wherein the step of receiving user input further includes:

providing a first graphical user interface for prompting the user to input a first joint point and a second joint point; and receiving the first joint point and the second joint point; and wherein the step of automatically re-calculating the contour of the target bone includes the step of automatically re-calculating the contour of the target bone based on the first joint point and the second joint point.

17. The method of claim 15 wherein the step of receiving user input further includes providing a second graphical user interface for prompting the user to activate one of an top up button, a top down button, a bottom up button, and a bottom down button; wherein each button has an associated button signal; and receiving the activated button signal;

and wherein the step of automatically re-calculating the contour of the target bone includes the step of automatically re-calculating the contour of the target bone based on the activated button signal.

18. The method of claim 14 further comprising:

determining if the displayed contour meets predetermined standards;

if yes, determining the bone density measurement based on the target bone contour;

else prompting the user for input, automatically re-calculating the contour of the target bone based on the user input, and automatically displaying the recalculated contour; and proceeding to the step of determining if the displayed contour meets predetermined standards.

19. The method of claim 14 wherein the bone contour is a closed contour, said method further comprising the steps of:

a) defining a contour based coordinate system;

b) dividing the bone contour into phases;

c) for each phase, accumulating all pixel values in the phase while subtracting those pixel values attributable to soft tissue to determine the mass of the bone; and d) summing the mass of each phase to generate a total mass;

e) for each phase determining the volume of the phase;

f) summing the volume of each phase to generate a total volume g) dividing the total mass of the bone by the total volume of the bone to determine the bone mass density of the bone.

20. The method of claim 19 further comprising:

a) rotating the bone contour after receiving the bone contour.

* * * * *